United States Patent [19]
Lal et al.

[11] Patent Number: 5,932,445
[45] Date of Patent: Aug. 3, 1999

[54] SIGNAL PEPTIDE-CONTAINING PROTEINS

[75] Inventors: Preeti Lal, Santa Clara; Janice Au-Young, Berkeley; Roopa Reddy, Sunnyvale; Lynn E. Murry, Portola Valley; Preete Mathur, Fremont, all of Calif.

[73] Assignee: Incyte Pharmaceuticals, Inc., Palo Alto, Calif.

[21] Appl. No.: 08/966,316

[22] Filed: Nov. 7, 1997

[51] Int. Cl.⁶ .............................. C07H 21/00; C12N 1/13; C12N 5/10; C12N 15/63

[52] U.S. Cl. .................... 435/69.1; 435/69.8; 435/320.1; 435/252.3; 435/325; 536/23.5

[58] Field of Search .................................. 435/69.1, 69.8, 435/471, 476, 325, 252.3; 536/23.1, 23.5

[56] References Cited

PUBLICATIONS

Pearson, W.R, et al., "Improved tools for biological sequence comparison", *Proc. Natl. Acad. Sci. USA*, 85:2444–2448 (1988).

Smith, T.F. and M.S. Waterman, "Identification of Common Molecular Subsequences", *J. Mol. Biol.*, 147:195–197 (1981).

Krogh, A., et al., "Hidden Markov Models in Computational Biology. Applications to Protein Modeling", *J. Mol. Biol.*, 235:1501–1531 (1994).

Stultz, C.M., "Structural analysis based on state–space modeling", *Protein Sci.*, 2:305–314 (1993).

Bolander, F.F., et al., "Serpentine Receptors", *Molecular Endocrinology Second Edition*, 162–176 (1994).

Stosberg, A.D., "Structure/function relationship of proteins belonging to the family of receptors coupled to GTP–binding proteins", *Eur. J. Biochem.*, 196:1–10 (1991).

Hardie, G., and T. Hunter, "The Eukaryotic Protein Kinase Superfamily", *The Protein Kinase FactsBook, Protein–Serine Kinases*, Chapter 2 pp. 7–21 (1992).

McGowan, S.E., "Extracellular matrix and the regulation of lung development and repair", *FASEB J.*, 6:2895–2904 (1992).

Engel, J., et al., "Domain organizations of extracellular matrix proteins and their evolution", *Development 1994 Supplement*, 35–42 (1994).

Soltysik–Espanola, M., et al., "Endo 16, a Large Multidomain Protein Found on the Surface and ECM of Endodermal Cells during Sea Urchin Gastrulation, Binds Calcium", *Dev. Biol.*, 165:73–85 (1994).

Kragh–Hansen, U., "Structure and ligand binding properties of human serum albumin", *Dan. Med. Bull.*, 37:57–84 (1990).

Colombatti, A. and P. Bonaldo, "The Superfamily of Proteins with von Willebrand Factor Type A–like Domains: One Theme Common to Components of Extracellular Matrix Hemostasis, Cellular Adhesion, and Defense Mechanisms", *Blood*, 77:2305–2315 (1991).

Lee, J.O., et al., "Crystal Structure of the A Domain from the A Subunit of Integrin CR3 (CD11b/CD18)", *Cell*, 80:631–638 (1995).

Roman, J., "Extracellular Matrix and Lung Inflammation", *Immunol. Res.*, 15:163–178 (1996).

Nielsen, M.D., et al., "Differential Regulation of Type I and Type VIII $Ca^{2+}$–stimulated Adenylyl Cyclases by $G_i$–coupled Receptors in Vivo", *J. Biol. Chem.*, 271:33308–33316 (1996).

Hellevuo, K., et al, "The Characterization of a Novel Human Adenylyl Cyclase Which Is Present in Brain and Other Tissues", *J. Biol. Chem.*, 270:11581–11589 (1995).

Robson, S.C., et al., "Loss of ATP Diphosphohydrolase Activity with Endothelial Cell Activation", *J. Exp. Med.*, 185:153–163 (1997).

Matsuoka, I., et al., (GI 399710) GenBank Sequence Database (Accession S63848), National Center for Biotechnology Information: National Library of Medicine, Bethesda, Maryland 20849. (GI 399711) (1993).

Groden, J., et al., "Response of Colon Cancer Cell Lines to the Introduction of APC, a Colon–specific Tumor Suppressor Gene[1]", *Cancer. Res.*, 55:1531–1539 (1995).

Erb, L., et al., "Functional expression and photoaffinity labeling of a cloned $P_{2U}$ purinergic receptor", *Proc. Natl. Acad. Sci. USA*, 90:10449–10453 (1993).

O'Dowd, B.F. et al. *FEBS Letters* 394: 325–329 (1996).

Li, M.–S. et al. *Biochem. J.* 305: 921–927 (1995).

Sreedhavan, S.P. et al. *PNAS* 88:4986–4990 (1991).

Matsuoka, I. et al. *Biochem. Biophys. Res. Comm.* 194(1):504–511 (1993).

*Primary Examiner*—Dian C. Jacobson
*Attorney, Agent, or Firm*—Incyte Pharmaceuticals, Inc.; Lynn E. Murry

[57] ABSTRACT

The invention provides signal peptide-containing proteins collectively designated SP, and polynucleotides which identify and encode these molecules. The invention also provides expression vectors, host cells, agonists, antibodies and antagonists. The invention further provides methods for diagnosing, treating, and preventing disorders associated with expression of signal peptide-containing proteins.

9 Claims, 6 Drawing Sheets

```
5' NGC GAC GTA CAA CAG ATT GGA GCC ATG GCT TTG GAA CAG AAC CAG TCA ACA GAT
                                    M   A   L   E   Q   N   Q   S   T   D
    9          18          27          36          45          54

TAT TAT TAT GAG GAA AAT GAA ATG AAT GGC ACT TAT GAC TAC AGT CAA TAT GAA
 Y   Y   Y   E   E   N   E   M   N   G   T   Y   D   Y   S   Q   Y   E
    63          72          81          90          99         108

CTG ATC TGT ATC AAA GAA GAT GTC AGA GAA TTT GCA AAA GTT TTC CTC CCT GTA
 L   I   C   I   K   E   D   V   R   E   F   A   K   V   F   L   P   V
   117         126         135         144         153         162

TTC CTC ACA ATA GTT TTC GTC ATT GGA CTT GCA AAT TCC ATG GTA GTG GCA
 F   L   T   I   V   F   V   I   G   L   A   N   S   M   V   V   A
   171         180         189         198         207         216

ATT TAT GCC TAT TAC TAC AAG AAA CAG AGA ACC AAA ACA GAT GTG TAC ATC CTG AAT
 I   Y   A   Y   Y   Y   K   K   Q   R   T   K   T   D   V   Y   I   L   N
   225         234         243         252         261         270

TTC CTC ACA ATA GTT TTA CTC CTT CTA TTC ACT CTG CCT TTT TGG GCT GTT AAT
                 L   L   F   T   L   P   F   W   A   V   N
   279         288         297         306         315         324
```

FIGURE 1A

```
      333         342         351         360         369         378
GCA GTT CAT GGG TGG GTT TTA GGG AAA ATA ATG TGC AAA ATA ACT TCA GCC TTG
 A   V   H   G   W   V   L   G   K   I   M   C   K   I   T   S   A   L 387         396         405         414         423         432
TAC ACA CTA AAC TTT GTC TCT GGA ATG CAG TTT CTG GCT TGT ATC AGC ATA GAC
 Y   T   L   N   F   V   S   G   M   Q   F   L   A   C   I   S   I   D 441         450         459         468         477         486
AGA TAT GTG GCA GTA ACT AAA GTC CCC AGC CAA TCA GGA GTG AAA CCA TGC
 R   Y   V   A   V   T   K   V   P   S   Q   S   G   V   K   P   C 495         504         513         522         531         540
TGG ATC ATC TGT TTC TGT GTC TGG ATG GCT GCC ATC TTG CTG AGC ATA CCC CAG
 W   I   I   C   F   C   V   W   M   A   A   I   L   L   S   I   P   Q 549         558         567         576         585         594
CTG GTT TTT TAT ACA TGT TGT GTA AAT GAC AAT GCT AGG TGC ATT TTC CCC CGC
 L   V   F   Y   T   C   C   V   N   D   N   A   R   C   I   F   P   R 603         612         621         630         639         648
TAC CTA GGA ACA TCA ACA ATG AAA GCA TTG ATT CAA ATG CTA GAG CTA TGC ATT GGA
 Y   L   G   T   S   T   M   K   A   L   I   Q   M   L   E   L   C   I   G
```

FIGURE 1B

```
TTT GTA CCC TTT ATT ATG GGG GTG TGC TAC TTT ATC ACA GCA AGG ACA
                                                                   657                                                          702
 F   V   P   F   I   M   G   V   C   Y   F   I   T   A   R   T

CTC ATG AAG ATG CCA AAC ATT AAA ATA TCT CGA CCC CTA AAA GTT CTG CTC ACA
                                                                   711                                                          756
 L   M   K   M   P   N   I   K   I   S   R   P   L   K   V   L   L   T

GTC GTT ATA GTT TTC ATT GTC ACT CAA CTG CCT ATC TAT AAC ATT GTC AAG TTC TGC
                                                                   765                                                          810
 V   V   I   V   F   I   V   T   Q   L   P   Y   N   I   V   K   F   C

CGA GCC ATA GAC ATC ATC TAC TCC CTG ATC ACC AGC TGC AAC ATG AGC AAA CGC
                                                                   819                                                          864
 R   A   I   D   I   I   Y   S   L   I   T   S   C   N   M   S   K   R

ATG GAC ATC GCC ATC CAA GTC ACA GAA AGC ATC GCA CTC TTT CAC AGC TGC CTC
                                                                   873                                                          918
 M   D   I   A   I   Q   V   T   E   S   I   A   L   F   H   S   C   L

AAC CCA ATC CTT TAT GTT TTT ATG GGA GCA TCT TTC AAA AAC TAC GTT ATG AAA
                                                                   927                                                          972
 N   P   I   L   Y   V   F   M   G   A   S   F   K   N   Y   V   M   K
```

FIGURE 1C

```
      981          990          999         1008         1017         1026
GTG GCC AAG AAA TAT GGG TCC TGG AGA AGA CAG AGA CAA AGT GTG GAG GAG TTT
 V   A   K   K   Y   G   S   W   R   R   Q   R   Q   S   V   E   E   F 1035         1044         1053         1062         1071         1080
CCT TTT GAT TCT GAG GGT CCT ACA GAG CCA ACC AGT ACT TTT AGC ATT TAA AGG
 P   F   D   S   E   G   P   T   E   P   T   S   T   F   S   I 1089         1098         1107         1116         1125         1134
TAA AAC TGC TCT GCC TTT TGC TTG GAT ACA TAT GAA TGA TGC TTT CCC CTC AAA 1143         1152         1161         1170         1179         1188
TAA AAC ATC TGC ATT ATT CTG AAA CTC AAA TCT CAG ACG CCG TGG TTG CAA CTT 1197         1206         1215         1224         1233         1242
ATA ATA AAG AAT GGG TTG GGG GAA GGA GAA ATA AAA GCC AAG AAG AGG AAA 1251         1260         1269         1278         1287         1296
CAA GAT AAT AAA TGT ACA AAA CAT GAA AAT TAA AAT GAA CAA TAT AGG AAA ATA 1305         1314         1323         1332         1341         1350
ATT GTA ACA GGC ATA AGT GAA TAA CAC TCT GCT GTA ACG AAG AAG AGC TTT GTG
```

FIGURE 1D

```
     1359            1368            1377            1386            1395            1404
GTG ATA ATT TTG TAT CTT GGT TGC AGT GGT GCT TAT ACA AAT CTA CAC AAG TGA
     1413            1422            1431            1440            1449            1458
TAA AAT GAC AGA GAA CTA TAT ACA CAC ATT GTA CCA ATT TCA ATT TCC TGG TTT
     1467            1476            1485            1494            1503            1512
TGA CAT TAT AGT ATA ATT ATG TAA GAT GGA ACC ATT GGG GAA AAC TGG GTG AAG
     1521            1530            1539            1548            1557            1566
GGT ACC CAG GAC CAC TCT GTA CCA TCT TTG TAA CTT CCT GTG AAT TTA TAA TAA
     1575            1584            1593            1602            1611            1620
TTT CAA AAT AAA ACA AGT TAA AAA AAC CCA CTA TGC TAT AAG TTA GGC CAT
     1629            1638            1647            1656
CTA AAA CAG ATT ATT AAA GAG GTT CAT GTT AAA AGG CAT GC 3'
```

SIGNAL PEPTIDE-CONTAINING PROTEINS

FIELD OF THE INVENTION

This invention relates to nucleic acid and amino acid sequences of new signal peptide-containing proteins which are important in disease and to the use of these sequences in the diagnosis, treatment, and prevention of diseases associated with cell proliferation and cell signaling.

BACKGROUND OF THE INVENTION

Protein transport is a quintessential process for both prokaryotic and eukaryotic cells. Transport of an individual protein usually occurs via an amino-terminal signal sequence which directs, or targets, the protein from its ribosomal assembly site to a particular cellular or extracellular location. Transport may involve any combination of several of the following steps: contact with a chaperone, unfolding, interaction with a receptor and/or a pore complex, addition of energy, and refolding. Moreover, an extracellular protein may be produced as an inactive precursor. Once the precursor has been exported, removal of the signal sequence by a signal peptidase activates the protein.

Although amino-terminal signal sequences vary substantially, many patterns and overall properties are shared. Recently, hidden Markov models (HMMs), statistical alternatives to FASTA and Smith Waterman algorithms, have been used to find shared patterns, specifically consensus sequences (Pearson, W. R. and D. J. Lipman (1988) Proc. Natl. Acad. Sci. 85:2444–2448; Smith, T. F. and M. S. Waterman (1981) J. Mol. Biol. 147:195–197). Although they were initially developed to examine speech recognition patterns, HMMs have been used in biology to analyze protein and DNA sequences and to model protein structure (Krogh, A. et al. (1994) J. Mol. Biol. 235:1501–1531; Collin, M. et al. (1993) Protein Sci. 2:305–314). HMMs have a formal probabilistic basis and use position-specific scores for amino acids or nucleotides and for opening and extending an insertion or deletion. The algorithms are quite flexible in that they incorporate information from newly identified sequences to build even more successful patterns. To find signal sequences, multiple unaligned sequences are compared to identify those which encode a peptide of 20 to 50 amino acids with an N-terminal methionine.

Some examples of the protein families which are known to have signal sequences are receptors (nuclear, 4 transmembrane, G protein coupled, and tyrosine kinase), cytokines (chemokines), hormones (growth and differentiation factors), neuropeptides and vasomediators, protein kinases, phosphatases, phospholipases, phosphodiesterases, nucleotide cyclases, matrix molecules (adhesion, cadherin, extracellular matrix molecules, integrin, and selectin), G proteins, ion channels (calcium, chloride, potassium, and sodium), proteases, transporter/pumps (amino acid, protein, sugar, metal and vitamin; calcium, phosphate, potassium, and sodium) and regulatory proteins. Descriptions of some of these proteins (receptors, kinases, and matrix proteins) and diseases associated with their dysfunction follow.

G-protein coupled receptors (GPCR) are a large group of receptors which transduce extracellular signals. GPCRs include receptors for biogenic amines such as dopamine, epinephrine, histamine, glutamate (metabotropic effect), acetylcholine (muscarinic effect), and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and thrombin; and for sensory signal mediators such as retinal photopigments and olfactory stimulatory molecules. The structure of these highly-conserved receptors consists of seven hydrophobic transmembrane regions, an extracellular N-terminus, and a cytoplasmic C-terminus. The N-terminus interacts with ligands, and the C-terminus interacts with intracellular G proteins to activate second messengers such as cyclic AMP (cAMP), phospholipase C, inositol triphosphate, or ion channel proteins. Three extracellular loops alternate with three intracellular loops to link the seven transmembrane regions. The most conserved parts of these proteins are the transmembrane regions and the first two cytoplasmic loops. A conserved, acidic-Arg-aromatic triplet present in the second cytoplasmic loop may interact with the G proteins. The consensus pattern, [Gly Ser Thr Ala Leu Ile Val Met Tyr Trp Cys]-[Gly Ser Thr Ala Asn Cys Pro Asp Glu]-{Glu Asp Pro Lys Arg His}-Xaa(2)-[Leu Ile Val Met Asn Gln Gly Ala]-Xaa(2)-[Leu Ile Val Met Phe Thr]-[Gly Ser Thr Ala Asn Cys]-[Leu Ile Val Met Phe Tyr Trp Ser Thr Ala Cys]-[Asp Glu Asn His]-Arg-[Phe Tyr Trp Cys Ser His]-Xaa(2)-[Leu Ile Val Met] is characteristic of most proteins belonging to this group (Bolander, F. F. (1994) *Molecular Endocrinology*, Academic Press, San Diego, Calif.; Strosberg, A. D. (1991) Eur. J. Biochem. 196:1–10).

The kinases comprise the largest known group of proteins, a superfamily of enzymes with widely varied functions and specificities. Kinases regulate many different cell proliferation, differentiation, and signaling processes by adding phosphate groups to proteins. Receptor mediated extracellular events trigger the transfer of these high energy phosphate groups and activate intracellular signaling cascades. Activation is roughly analogous to the turning on a molecular switch, and in cases where signalling is uncontrolled, may be associated with or produce inflammation and cancer.

Kinases are usually named after their substrate, their regulatory molecule, or after some aspect of a mutant phenotype. Almost all kinases contain a similar 250–300 amino acid catalytic domain. The N-terminal domain, which contains subdomains I-IV, generally folds into a two-lobed structure which binds and orients the ATP (or GTP) donor molecule. The larger C terminal lobe, which contains subdomains VIA-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (between 5 and 100 residues) located on either side of, or inserted into loops of, the kinase domain. These amino acid sequences allow the regulation of each kinase as it recognizes and interacts with its target protein. The primary structure of the kinase domain is conserved and contains specific residues and identifiable motifs or patterns of amino acids. The serine threonine kinases represent one family which preferentially phosphorylates serine or threonine residues. Many serine threonine kinases, including those from human, rabbit, rat, mouse, and chicken cells and tissues, have been described (Hardie, G. and Hanks, S. (1995) The Protein Kinase Facts Books, Vol I:7–20 Academic Press, San Diego, Calif.).

The matrix proteins (MPs) provide structural support, cell and tissue identity, and autocrine, paracrine and juxtacrine properties for most eukaryotic cells (McGowan, S. E. (1992) FASEB J. 6:2895–2904). MPs include adhesion molecules, integrins and selectins, cadherins, lectins, lipocalins, and extracellular matrix proteins (ECMs). MPs possess many different domains which interact with soluble, extracellular molecules. These domains include collagen-like domains, EGF-like domains, immunoglobulin-like domains, fibronectin-like domains, type A domain of von Willebrand factor (vWFA)-like modules, ankyrin repeat modules, RDG or RDG-like sequences, carbohydrate-binding domains, and calcium ion-binding domains.

For example, multidomain or mosaic proteins play an important role in the diverse functions of the ECMs (Engel, J. et al. (1994) Development S35–42). ECM proteins (ECMPs) are frequently characterized by the presence of one or more domains which may contain a number of potential intracellular disulphide bridge motifs. For example, domains which match the epidermal growth factor tandem repeat consensus are present within several known extracellular proteins that promote cell growth, development, and cell signaling. Other domains share internal homology and a regular distribution of single cysteines and cysteine doublets. In the serum albumin family, cysteine arrangement generates the characteristic 'double-loop' structure (Soltysik-Espanola, M. et al. (1994) Dev. Biol. 165:73–85) important for ligand-binding (Kragh-Hansen, U. (1990) Danish Med. Bull. 37:57–84). Other ECMPs are members of the vWFA-like module superfamily, a diverse group of proteins with a module sharing high sequence similarity. The vWFA-like module is found not only in plasma proteins but also in plasma membrane and ECMPs (Colombatti, A. and Bonaldo, P. (1991) Blood 77:2305–2315). Crystal structure analysis of an integrin vWFA-like module shows a classic "Rossmann" fold and suggests a metal ion-dependent adhesion site for binding protein ligands (Lee, J.-O. et al. (1995) Cell 80:631–638).

The diversity, distribution and biochemistry of MPs is indicative of their many, overlapping roles in cell proliferation and cell signaling. MPs function in the formation, growth, remodeling, and maintenance of bone, and in the mediation and regulation of inflammation. Biochemical changes that result from congenital, epigenetic, or infectious diseases affect the expression and balance of MPs. This balance, in turn, affects the activation, proliferation, differentiation, and migration of leukocytes and determines whether the immune response is appropriate or self-destructive (Roman, J. (1996) Immunol. Res. 15:163–178).

Adenylyl cyclases (AC) are a group of second messenger molecules which actively participate in cell signaling processes. There are at least eight types of mammalian ACs which show regions of conserved sequence and are responsive to different stimuli. For example, the neural-specific type I AC is a $Ca^{++}$-stimulated enzyme whereas the human type VII is unresponsive to $CA^{++}$ and responds to prostaglandin E1 and isoproterenol. Characterization of these ACs, their tissue distribution, and the activators and inhibitors of the different types of ACs is the subject of various investigations (Nielsen, M. D. et al. (1996) J. Biol. Chem. 271:33308–16; Hellevuo, K. et al. (1995) J. Biol. Chem. 270:11581–9). AC interactions with kinases and G proteins in the intracellular signaling pathways of all tissues make them interesting candidate molecules for pharmaceutical research.

ATP diphosphohydrolase (ATPDase) is an enzyme expressed and secreted by quiescent endothelial cells and involved in vasomediation. The physiological role of ATPDase is to convert ATP and ADP to AMP. When this conversion occurs in the blood vessels during inflammatory response, it prevents extracellular ATP from causing vascular injury by inhibiting platelet activation and modulating vascular thrombosis (Robson, S. C. et al. (1997) J. Exp. Med.185:153–63).

The discovery of new signal peptide-containing proteins and the polynucleotides encoding these molecules satisfies a need in the art by providing new compositions useful in the diagnosis, treatment, and prevention of diseases associated with cell proliferation and cell signaling, particularly cancer, immune response and neuronal disorders.

SUMMARY OF THE INVENTION

The invention features a substantially purified signal peptide-containing protein (SP) having an amino acid sequence selected from the group encoded by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:17.

The invention further provides isolated and substantially purified polynucleotide sequences encoding SP. In a particular aspect, the polynucleotide has a nucleic acid sequence selected from the group consisting of SEQ ID NOs:1–15 and 17.

In addition, the invention provides a polynucleotide sequence, or fragment thereof, which hybridizes to any of the polynucleotide sequences of SEQ ID NOs:1–15 and 17. In another aspect, the invention provides a composition comprising isolated and purified polynucleotide sequences of SEQ ID NOs:1–15 and 17, or a fragment thereof.

One aspect of the invention features an isolated and substantially purified polynucleotide which encodes SP-16. In a particular aspect, the polynucleotide is the nucleic acid sequence of SEQ ID NO:17. In another aspect, the polynucleotide is a fragment or an oligonucleotide comprising the nucleic acid sequence extending from $A_{24}$ to $G_{44}$, $G_{159}$ to $C_{182}$, $G_{561}$ to $A_{596}$, or $A_{1011}$ to $T_{1046}$ of SEQ ID NO:17.

The invention further provides a polynucleotide sequence comprising the complement, or fragments thereof, of any one of the polynucleotide sequences encoding SP. In another aspect, the invention provides compositions comprising isolated and purified polynucleotide sequences comprising the complements of SEQ ID NOs:1–15 and 17, or fragments thereof.

The present invention further provides an expression vector containing at least a fragment of any one of the polynucleotide sequences of SEQ ID NOs:1–15 and 17. In yet another aspect, the expression vector containing the polynucleotide sequence is contained within a host cell.

The invention also provides a method for producing a polypeptide or a fragment thereof, the method comprising the steps of: a) culturing the host cell containing an expression vector containing at least a fragment of the polynucleotide sequence encoding an SP under conditions suitable for the expression of the polypeptide; and b) recovering the polypeptide from the host cell culture.

The invention also provides a pharmaceutical composition comprising a substantially purified SP in conjunction with a suitable pharmaceutical carrier.

The invention also provides a purified antagonist of SP. In one aspect the invention provides a purified antibody which binds to an SP.

Still further, the invention provides a purified agonist of SP.

The invention also provides a method for treating or preventing a cancer, the method comprising the step of administering to a subject in need of such treatment an effective amount of a pharmaceutical composition containing SP.

The invention also provides a method for treating or preventing a cancer, the method comprising the step of administering to a subject in need of such treatment an effective amount of an antagonist of SP.

The invention also provides a method for treating or preventing a neuronal disorder, the method comprising the step of administering to a subject in need of such treatment an effective amount of an antagonist of SP.

The invention also provides a method for treating or preventing an immune response associated with the increased expression or activity of SP, the method comprising the step of administering to a subject in need of such treatment an effective amount of an antagonist of SP.

The invention also provides a method for stimulating cell proliferation, the method comprising the step of administering to a cell an effective amount of purified SP.

The invention also provides a method for detecting a nucleic acid sequence which encodes a signal peptide-containing protein in a biological sample, the method comprising the steps of: a) hybridizing a nucleic acid sequence of the biological sample to a polynucleotide sequence complementary to the polynucleotide encoding SP, thereby forming a hybridization complex; and b) detecting the hybridization complex, wherein the presence of the hybridization complex correlates with the presence of the nucleic acid sequence encoding the signal peptide-containing protein in the biological sample.

The invention also provides a microarray which contains at least a fragment of at least one of the polynucleotide sequences encoding SP. In a particular aspect, the microarray contains at least a fragment of at least one of the sequences selected from the group consisting of SEQ ID NOs:1–15 and 17.

The invention also provides a method for detecting the expression level of a nucleic acid sequence encoding a signal peptide-containing protein in a biological sample, the method comprising the steps of hybridizing the nucleic acid sequence of the biological sample to a complementary polynucleotide, thereby forming hybridization complex; and determining expression of the nucleic acid sequence encoding a signal peptide-containing protein in the biological sample by identifying the presence of the hybridization complex. In a preferred embodiment, prior to the hybridizing step, the nucleic acid sequences of the biological sample are amplified and labeled by the polymerase chain reaction.

BRIEF DESCRIPTION OF THE FIGURES

FIGS. 1A, 1B, 1C, 1D, and 1E show the amino acid sequence (SEQ ID NO:16) and nucleic acid sequence (SEQ ID NO:17) of SP16. The alignment was produced using MacDNASIS PRO software (Hitachi Software Engineering Co. Ltd. S. San Francisco Calif.).

FIG. 2 shows the amino acid sequence alignment between SP-16 (2547002; SEQ ID NO:16) and the bovine GPCR (GI 399711; SEQ ID NO:18) produced using the multisequence alignment program of LASERGENE software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, arrays and methodologies which are reported in the publications which might be used in connection with the invention. Nothing herein is to be construed as an admission that the invention is not entitled to antedate such disclosure by virtue of prior invention.

Definitions

SP, as used herein, refers to the amino acid sequences of substantially purified SP obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to SP, increases or prolongs the duration of the effect of SP. Agonists may include proteins, nucleic acids, carbohydrates, or any other molecules which bind to and modulate the effect of SP.

An "allele" or "allelic sequence", as used herein, is an alternative form of the gene encoding SP. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding SP, as used herein, include those with deletions, insertions, or substitutions of different nucleotides resulting in a polynucleotide that encodes the same or a functionally equivalent SP. Included within this definition are polymorphisms which may or may not be readily detectable using a particular oligonucleotide probe of the polynucleotide encoding SP, and improper or unexpected hybridization to alleles, with a locus other than the normal chromosomal locus for the polynucleotide sequence encoding SP. The encoded protein may also be "altered" and contain deletions, insertions, or substitutions of amino acid residues which produce a silent change and result in a functionally equivalent SP. Deliberate amino acid substitutions may be made on the basis of similarity in polarity, charge, solubility, hydrophobicity, hydrophilicity, and/or the amphipathic nature of the residues as long as the biological or immunological activity of SP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of SP are preferably about 5 to about 15 amino acids in length and retain the biological activity or the immunological activity of SP. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to SP, decreases the amount or the duration of the effect of the biological or immunological activity of SP. Antagonists may include proteins, nucleic acids, carbohydrates, or any other molecules which decrease the effect of SP.

As used herein, the term "antibody" refers to intact molecules as well as fragments thereof, such as Fa, $F(ab')_2$, and Fv, which are capable of binding the epitopic determinant. Antibodies that bind SP polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic SP, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding SP (SEQ ID NOs:1–15 and 17) or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of a ribonucleic acid that is similar to a polynucleotide encoding an SP by northern analysis is indicative of the presence of mRNA encoding SP in a sample and thereby correlates with expression of the transcript from the polynucleotide encoding the protein.

The term "SP" refers to any or all of the human polypeptides, SP-1, SP-2, SP-3, SP-4, SP-5, SP-6, SP-7, SP-8, SP-9, SP-10, SP-11, SP-12, SP-13, SP-14, SP-15, and SP-16.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to SP or the encoded SP. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permnitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat. Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

"Inflammation", as used herein, is interchangeable with "immune response", both terms refer to a condition associated with trauma, immune disorders, and infectious or genetic diseases and are characterized by production of cytokines, chemokines, and other signaling molecules which activate cellular and systemic defense systems.

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct oligonucleotides arranged on a substrate, such as paper, nylon or other type of membrane, filter, gel, polymer, chip, glass slide, or any other suitable support.

The term "modulate", as used herein, refers to a change in the activity of SP. For example, modulation may cause an increase or a decrease in protein activity, binding characteristics, or any other biological, functional or immunological properties of SP.

"Nucleic acid sequence", as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of an SP encompasses the full-length SP and fragments thereof.

The term "sample", as used herein, is used in its broadest sense. A biological sample suspected of containing nucleic acid encoding SP, or fragments thereof, or SP itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

SEQ ID NO:10, SEQ ID NO:11, SEQ ID NO:12, SEQ ID NO:13, SEQ ID NO:14, SEQ ID NO:15, and SEQ ID NO:17), and the use of these compositions for the diagnosis, treatment or prevention of diseases associated with cell proliferation and cell signaling. Table 1 shows the sequence identification numbers, reference, Incyte Clone number, cDNA library, NCBI sequence identifier and GenBank description for each of the signal peptide-containing proteins disclosed herein.

TABLE 1

| SEQUENCES | DESIGNATION | INCYTE CLONE | LIBRARY | HOMOLOG | GENBANK DESCRIPTOR |
|---|---|---|---|---|---|
| SEQ ID NO:1 | SP-1 | 1221102 | NEUTGMT01 | g1575512 | GPR19 gene |
| SEQ ID NO:2 | SP-2 | 1457779 | COLNFET02 | g1842120 | ATP diphosphohydrolase |
| SEQ ID NO:3 | SP-3 | 1682433 | PROSNOT15 | g1070391 | transmembrane protein |
| SEQ ID NO:4 | SP-4 | 1899132 | BLADTUT06 | g887602 | Saccharomyces cerevisiae protein |
| SEQ ID NO:5 | SP-5 | 1907344 | CONNTUT01 | g33715 | immunoglobulin light chain |
| SEQ ID NO:6 | SP-6 | 1963651 | BRSTNOT04 | g1657623 | orphan receptor RDC1 |
| SEQ ID NO:7 | SP-7 | 1976095 | PANCTUT02 | g2117185 | Mycobacterium tuberculosis protein |
| SEQ ID NO:8 | SP-8 | 2417676 | HNT3AZT01 | g2150012 | human transmembrane protein |
| SEQ ID NO:9 | SP-9 | 1805538 | SINTNOT13 | g294502 | extracellular matrix protein |
| SEQ ID NO:10 | SP-10 | 1869688 | SKINBIT01 | g1562 | G3 serine/threonine kinase |
| SEQ ID NO:11 | SP-11 | 1880692 | LEUKNOT03 | g1487910 | Caenorhabditis elegans protein |
| SEQ ID NO:12 | SP-12 | 318060 | EOSIHET02 | g606788 | opioid receptor |
| SEQ ID NO:13 | SP-13 | 396450 | PITUNOT02 | g342279 | opiomelanocortin |
| SEQ ID NO:14 | SP-14 | 506333 | TMLR3DT02 | g2204110 | adenylyl cyclase type VII |
| SEQ ID NO:15 | SP-15 | 764465 | LUNGNOT04 | g1902984 | lectin-like oxidized LDL receptor |
| SEQ ID NO:16 | SP-16 | 2547007 | UTRSNOT11 | g399711 | bovine GPCR |
| SEQ ID NO:17 | | 2547007 | UTRSNOT11 | | |

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformned" cells include stably transformed cells in which the inserted DNA is capable of replication either as an autonomously replicating plasmid or as part of the host chromosome. They also include cells which transiently express the inserted DNA or RNA for limited periods of time.

A "variant" of SP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The Invention

The invention is based on the discovery of signal peptide-containing proteins, collectively referred to as SP and individually as SP-1, SP2, SP-3, Sp-4, SP-5, SP-6, SP-7, SP-8, SP-9, SP-10, SP-11, SP-12, SP-13, SP-14, SP-15, and SP-16, the polynucleotides encoding SP (SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SP-1 was identified in Incyte Clone 1221102 from the NEUTGMT01 cDNA library using a computer search for amino acid sequence alignments. A nucleotide sequence, SEQ ID NO:1, derived from Incyte Clone 1221102 encodes a GPCR with homology to GI 1575512, the GPR19 gene. Electronic northern analysis showed the expression of this sequence in neuronal tissues and in stimulated granulocytes.

SP-2 was identified in Incyte Clone 1457779 from the COLNFET02 cDNA library using a computer search for amino acid sequence alignments. A nucleotide sequence, SEQ ID NO:2, derived from Incyte Clone 1457779 encodes an ATP diphosphohydrolase with homology to GI 1842120. Electronic northern analysis showed the expression of this sequence in fetal colon.

SP-3 was identified in Incyte Clone 1682433 from the PROSNOT15 cDNA library using a computer search for amino acid sequence alignments. A nucleotide sequence, SEQ ID NO:3, derived from Incyte Clone 1682433 encodes a signal peptide-containing protein with homology to GI 1070391, a transmembrane protein. Electronic northern analysis showed the expression of this sequence in fetal, cancerous or inflamed cells and tissues. In particular, it was associated with cancerous prostate, asthmatic lung, promonocytes and IL-5 stimulated mononuclear cells.

SP-4 was identified in Incyte Clone 1899132 from the BLADTUT06 cDNA library using a computer search for amino acid sequence alignments. A nucleotide sequence, SEQ ID NO:4, derived from Incyte Clone 1899132 encodes a signal peptide containing protein with homology to GI 887602, a Saccharomyces cerevisiae protein. Electronic northern analysis showed the expression of this sequence in inflamed cells and tissues (62%) and cancerous tissues (25%). In particular, it was associated with stimulated promonocyte and mononuclear cells.

SP-5 was identified in Incyte Clone 1907344 from the CONNTUT01 cDNA library using a computer search for amino acid sequence alignments. A nucleotide sequence, SEQ ID NO:5, derived from Incyte Clone 1907344 encodes a signal peptide containing protein with homology to GI 33715, immunoglobulin light chain. Electronic northern analysis showed the expression of this sequence in cancerous tissues (66%), fetal or infant cells and tissues (22%).

SP-6 was identified in Incyte Clone 1963651 from the BRSTNOT04 cDNA library using a computer search for amino acid sequence alignments. A nucleotide sequence, SEQ ID NO:6, derived from Incyte Clone 1963651 encodes a GPCR with homology to GI 1657623, orphan receptor RDC1. Electronic northern analysis showed the expression of this sequence only in BRSTNOT04, tissue associated with a ductal carcinoma removed during mastectomy.

SP-7 was identified in Incyte Clone 1976095 from the PANCTUT02 cDNA library using a computer search for amino acid sequence alignments. A nucleotide sequence, SEQ ID NO:7, derived from Incyte Clone 1976095 encodes a signal peptide-containing protein with homology to GI 2117185, a *Mycobacterium tuberculosis* protein. Electronic northern analysis showed the expression of this sequence in cancerous (50%) and inflamed (30%) tissues.

SP-8 was identified in Incyte Clone 2417676 from the HNT3AZT01 cDNA library using a computer search for amino acid sequence alignments. A nucleotide sequence, SEQ ID NO:8, derived from Incyte Clone 2417676 encodes a signal peptide-containing protein with homology to GI 2150012, a human transmembrane protein. Electronic northern analysis showed this sequence to be expressed widely in proliferating, cancerous or inflamed tissues.

SP-9 was identified in Incyte Clone 1805538 from the SINTNOT13 cDNA library using a computer search for amino acid sequence alignments. A nucleotide sequence, SEQ ID NO:9, derived from Incyte Clone 1805538 encodes a signal peptide-containing protein with homology to GI 294502, an extracellular matrix protein. Electronic northern analysis showed this sequence to be expressed in inflamed tissues (87%).

SP-10 was identified in Incyte Clone 1869688 from the SKINBIT01 cDNA library using a computer search for amino acid sequence alignments. A nucleotide sequence, SEQ ID NO:10, derived from Incyte Clone 1869688 encodes a signal peptide-containing protein with homology to GI 1562, a G3 serine/threonine kinase. Electronic northern analysis showed this sequence to be expressed widely in proliferating fetal and inflamed tissues.

SP-11 was identified in Incyte Clone 1880692 from the LEUKNOT03 cDNA library using a computer search for amino acid sequence alignments. A nucleotide sequence, SEQ ID NO:11, derived from Incyte Clone 1880692 encodes a signal peptide-containing protein with homology to GI 1487910, a *Caenorhabditis elegans* protein. Electronic northern analysis showed this sequence to be expressed in cancer and blood cells.

SP-12 was identified in Incyte Clone 318060 from the EOSIHET02 cDNA library using a computer search for amino acid sequence alignments. A nucleotide sequence, SEQ ID NO:12, derived from Incyte Clone 318060 encodes a receptor with homology to GI 606788, an opioid GPCR. Electronic northern analysis showed this sequence to be expressed in inflamed nerve and blood cells.

SP-13 was identified in Incyte Clone 396450 from the PITUNOT02 cDNA library using a computer search for amino acid sequence alignments. A nucleotide sequence, SEQ ID NO:13, derived from Incyte Clone 396450 encodes a signal peptide-containing protein with homology to GI 342279, opiomelanocortin. Electronic northern analysis showed this sequence to be expressed in hormone producing cells and tissues (78%) and inflamed cells and tissues (45%).

SP-14 was identified in Incyte Clone 506333 from the TMLR3DT02 cDNA library using a computer search for amino acid sequence alignments. A nucleotide sequence, SEQ ID NO:14, derived from Incyte Clone 506333 encodes a signal peptide-containing protein with homology to GI 2204110, adenylyl cyclase. Electronic northern analysis showed this sequence to be expressed widely in cancerous and inflamed cells and tissues.

SP-15 was identified in Incyte Clone 764465 from the LUNGNOT04 cDNA library using a computer search for amino acid sequence alignments. A nucleotide sequence, SEQ ID NO:15, derived from Incyte Clone 764465 encodes a receptor with homology to GI 1902984, lectin-like oxidized LDL receptor. Electronic northern analysis showed this sequence to be expressed in lung and in fetal liver.

SP-16 (SEQ ID NO:16) was identified in Incyte Clone 2547002 from the UTRSNOT11 cDNA library using a computer search for amino acid sequence alignments. A consensus sequence, SEQ ID NO:17, was derived from the extension and assembly of the overlapping nucleic acid sequences of Incyte Clones 2741185 (BRSTTUT14), 2547002 (UTRSNOT11), and shotgun sequences, SAEA01463, SAEA01125, and SAEA00333.

Figure 2:
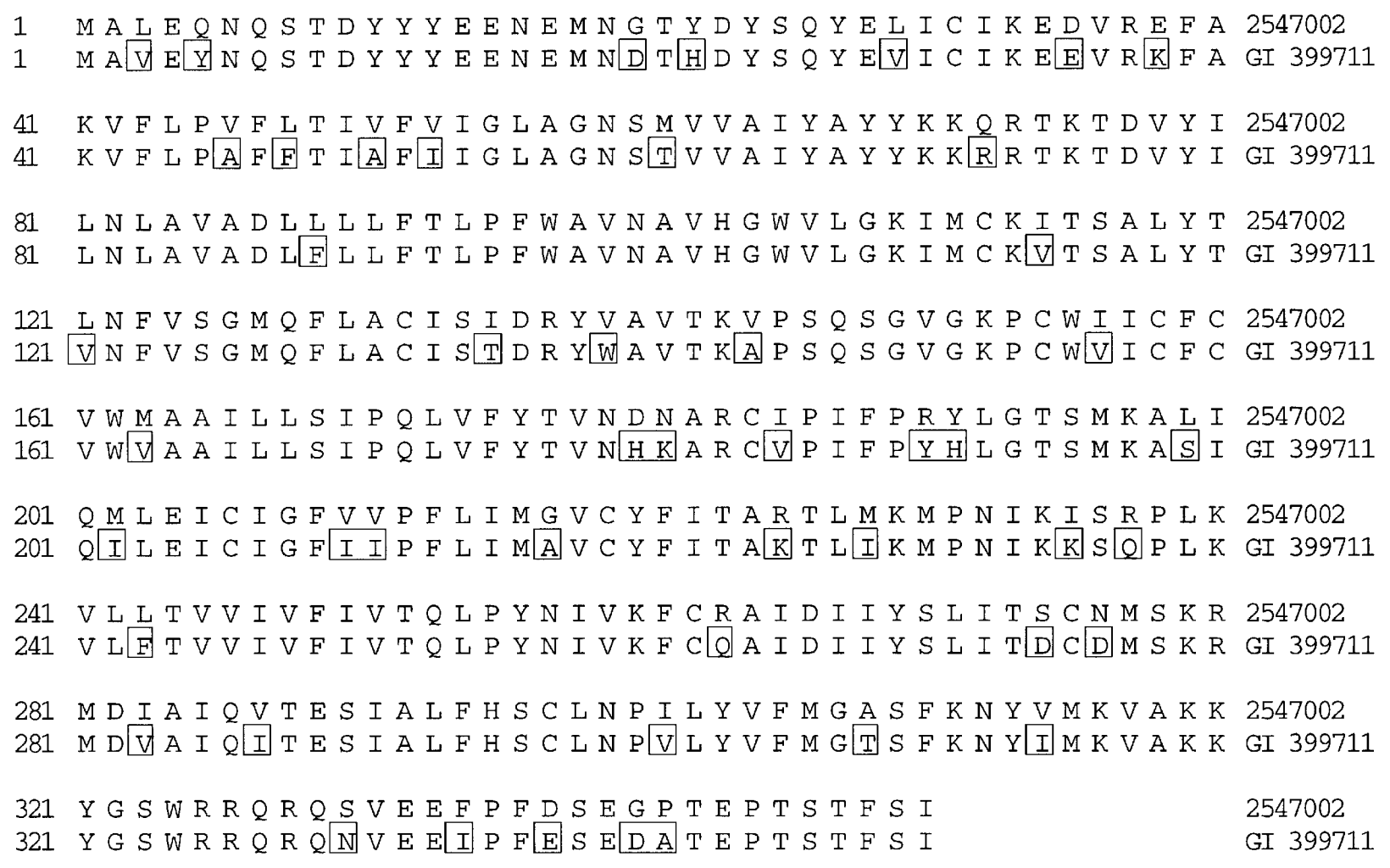

In one embodiment, the invention encompasses a polypeptide comprising the amino acid sequence of SEQ ID NO:16, as shown in FIG. 1A, 1B, 1C, 1D, and 1E. SP-16 is 350 amino acids in length and has a G protein coupled receptor signature at $Ser_{125}$ Gly Met Gln Phe Lue Ala Cys Ile Ser Ile Asp Arg Tyr Val Ala Val; three potential N-glycosylation sites at $N_6$, $N_{19}$, and $N_{276}$; a potential glycosaminoglycan attachment site at $S_{148}$; and ten potential phosphorylation sites at $S_{25}$, $T_{74}$, $T_{177}$, $S_{195}$, $T_{223}$, $Y_{269}$, $S_{278}$, $S_{309}$, $S_{323}$, and $S_{330}$. SP-16 has 86% sequence identity with a bovine GPCR (GI 399711) and shares the GPCR signature, the N-glycosylation, the glycosaminoglycan attachment site, and the first nine of the phosphorylation sites with the bovine receptor (FIG. 2). Fragments of the nucleic acid sequence useful for designing oligonucleotides or to be used directly as hybridization probes to distinguish between these homologous molecules include $A_{24}$ to $G_{44}$, $G_{159}$ to $C_{182}$, $G_{561}$ to $A_{596}$, or $A_{1011}$ to $T_{1046}$. mRNA encoding SP-16 was expressed in cDNA libraries with inflamed smooth muscle cells, uterus (38%) and heart and blood vessel (38%).

The invention also encompasses SP variants which retain the biological or functional activity of SP. A preferred SP variant is one having at least 80%, and more preferably 90%, amino acid sequence identity to the SP amino acid sequence. A most preferred SP variant is one having at least 95% amino acid sequence identity to an SP disclosed herein.

The invention also encompasses polynucleotides which encode SP. Accordingly, any nucleic acid sequence which encodes the amino acid sequence of SP can be used to produce recombinant molecules which express SP. In a particular embodiment, the invention encompasses a polynucleotide consisting of a nucleic acid sequence selected from the group consisting of SEQ ID NOs:1–15 and 17.

It will be appreciated by those skilled in the art that as a result of the degeneracy of the genetic code, a multitude of nucleotide sequences encoding SP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring SP, and all such variations are to be considered as being specifically disclosed.

Although nucleotide sequences which encode SP and its variants are preferably capable of hybridizing to the nucleotide sequence of the naturally occurring SP under appropriately selected conditions of stringency, it may be advantageous to produce nucleotide sequences encoding SP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding SP and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode SP and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding SP or any fragment thereof.

Also encompassed by the invention are polynucleotide sequences that are capable of hybridizing to the claimed nucleotide sequences, and in particular, those shown in SEQ ID NOs:1–15 and 17, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq polymerase (Perkin Elmer), thermostable T7 polymerase Amersham Pharmacia Biotech (Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding SP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries (Clontech, Palo Alto, Calif.) to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode SP may be used in recombinant DNA molecules to direct expression of SP, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express SP.

As will be understood by those of skill in the art, it may be advantageous to produce SP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter SP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding SP may be ligated to a heterologous sequence to encode a fusion protein. For example, to screen peptide libraries for inhibitors of SP activity, it may be useful to encode a chimeric SP protein that can be recognized by a commercially available antibody. A fusion protein may also be engineered to contain a cleavage site located between the SP encoding sequence and the heterologous protein sequence, so that SP may be cleaved and purified away from the heterologous moiety.

In another embodiment, sequences encoding SP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of SP, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of SP, or any part thereof, may be altered during direct synthesis and/or combined using chemical methods with sequences from other proteins, or any part thereof, to produce a variant polypeptide.

In order to express a biologically active SP, the nucleotide sequences encoding SP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding SP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding SP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell Systems, promoters from mammalian genes or from mammalian viruses are preferable. If it is necessary to generate a cell line that contains multiple copies of the sequence encoding SP, vectors based on SV40 or EBV may be used with an appropriate selectable marker.

In bacterial systems, a number of expression vectors may be selected depending upon the use intended for SP. For example, when large quantities of SP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding SP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding SP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs., S. or Murry, L. E. in McGraw Hill *Yearbook of Science and Technology* (1992) McGraw Hill, New York, N.Y.; pp. 191–196).

An insect system may also be used to express SP. For example, in one such system, *Autographa californica* nuclear polyhedrosis virus (AcNPV) is used as a vector to express foreign genes in *Spodoptera frugiperda* cells or in Trichoplusia larvae. The sequences encoding SP may be cloned into a non-essential region of the virus, such as the polyhedrin gene, and placed under control of the polyhedrin promoter. Successful insertion of SP will render the polyhedrin gene inactive and produce recombinant virus lacking coat protein. The recombinant viruses may then be used to infect, for example, *S. frugiperda* cells or Trichoplusia larvae in which SP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding SP may be ligated into an adenovirus transcription/translation complex consisting of the late promoter and tripartite leader sequence. Insertion in a non-essential E1 or E3 region of the viral genome may be used to obtain a viable virus which is capable of expressing SP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding SP. Such signals include the ATG initiation codon and adjacent sequences. In cases where sequences encoding SP, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express SP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14), and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being used widely not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding SP is inserted within a marker gene sequence, transformed cells containing sequences encoding SP can be identified by the absence of marker gene function. Alternatively, a marker gene can be placed in tandem with a sequence encoding SP under the control of a single promoter. Expression of the marker gene in response to induction or selection usually indicates expression of the tandem gene as well.

Alternatively, host cells which contain the nucleic acid sequence encoding SP and express SP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding SP can be detected by DNA-DNA or DNA-RNA hybridization or amplification using probes or fragments or fragments of polynucleotides encoding SP. Nucleic acid amplification based assays involve the use of oligonucleotides or oligomers based on the sequences encoding SP to detect transformants containing DNA or RNA encoding SP.

A variety of protocols for detecting and measuring the expression of SP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on SP is preferred, but a competitive binding assay may be employed. These and other assays are described, among other places, in Hampton, R. et al. (1990; Serological Methods, a laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding SP include oligolabeling, nick translation, end-labeling or PCR amplification using a labeled nucleotide. Alternatively, the sequences encoding SP, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding SP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode SP may be designed to contain signal sequences which direct secretion of SP through a prokaryotic or eukaryotic cell membrane. Other constructions may be used to join sequences encoding SP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and SP may be used to facilitate purification. One such expression vector provides for expression of a fusion protein containing SP and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992) Prot. Exp. Purif. 3: 263–281) while the enterokinase cleavage site provides a means for purifying SP from the fusion protein. A discussion of vectors which contain fusion proteins is provided in Kroll, D. J. et al. (1993; DNA Cell Biol. 12:441–453).

In addition to recombinant production, fragments of SP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of SP may be chemically synthesized separately and combined using chemical methods to produce the full length molecule.

Therapeutics

Chemical and structural homology exists among the signal peptide-containing proteins of the invention. The expression of SP is closely associated with cell proliferation and cell signaling. Therefore, in atherosclerosis, cancers, immune response, or neuronal disorders where SP is an activator, hormone, transcription factor, or any other signaling molecule which promotes cell proliferation or signaling; it is desirable to decrease the expression of SP. In cancers where SP is an inhibitor or suppressor and is controlling or decreasing cell proliferation, it is desirable to provide the protein or to increase the expression of SP.

In one embodiment, where SP is an inhibitor, SP or a fragment or derivative thereof may be administered to a subject to treat or prevent a cancer such as adenocarcinoma, leukemia, lymphoma, melanoma, myeloma, sarcoma, and teratocarcinoma. Such cancers include, but are not limited to, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising purified SP may be used to treat or prevent a cancer including, but not limited to, those listed above.

In another embodiment, an agonist which is specific for SP may be administered to a subject to treat or prevent a cancer including, but not limited to, those listed above.

In another further embodiment, a vector capable of expressing SP, or a fragment or a derivative thereof, may be administered to a subject to treat or prevent a cancer including, but not limited to, those listed above.

In a further embodiment where SP is promoting cell proliferation, antagonists which decrease the expression or activity of SP may be administered to a subject to treat or prevent a cancer such as adenocarcinoma, leukemia, lymphoma, melanoma, myeloma, sarcoma, and teratocarcinoma. Such cancers include, but are not limited to, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind SP may be used directly as an antagonist or indirectly as a targeting or delivery mechanism for bringing a pharmaceutical agent to cells or tissue which express SP.

In another embodiment, a vector expressing the complement of the polynucleotide encoding SP may be administered to a subject to treat or prevent a cancer including, but not limited to, those listed above.

In one embodiment, where SP is an activator or stimulates cell signaling, an antagonist of SP may be administered to a subject to treat or prevent a neuronal disorder. Such disorders may be include, but are not limited to akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

In another further embodiment, a vector expressing the complement of the polynucleotide encoding SP may be administered to a subject to treat or prevent a neuronal disorder, including, but not limited to, those listed above.

In yet another embodiment where SP is promoting cell proliferation, inflammation or immune response, antagonists which decrease the activity of SP may be administered to a subject to treat or prevent an immune response. Such responses may be associated with conditions and disorders such as atherosclerosis, AIDS, Addison's disease, adult respiratory distress syndrome, allergies, anemia, asthma, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections; and trauma. In particular, one aspect, antibodies which specifically bind SP may be used directly as an antagonist or indirectly as a targeting or delivery mechanism for bringing a pharmaceutical agent to cells or tissue which express SP.

In another embodiment, a vector expressing the complement of the polynucleotide encoding SP may be administered to a subject to treat or prevent an immune response including, but not limited to, those associated with the disorders listed above In one further embodiment, SP or a fragment or derivative thereof may be added to cells to stimulate cell proliferation. In particular, SP may be added to a cell in culture or cells in vivo using delivery mechanisms such as liposomes, viral based vectors, or electroinjection for the purpose of promoting cell proliferation and tissue or organ regeneration. Specifically, SP may be added to a cell, cell line, tissue or organ culture in vitro or ex vivo to stimulate cell proliferation for use in heterologous or autologous transplantation. In some cases, the cell will have been preselected for its ability to fight an infection or a cancer or to correct a genetic defect in a disease such as sickle cell anemia, β thalassemia, cystic fibrosis, or Huntington's chorea.

In another embodiment, an agonist which is specific for SP may be administered to a cell to stimulate cell proliferation, as described above.

In another embodiment, a vector capable of expressing SP, or a fragment or a derivative thereof, may be administered to a cell to stimulate cell proliferation, as described above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of SP may be produced using methods which are generally known in the art. In particular, purified SP may be used to produce antibodies or to screen libraries of pharmaceutical agents to identify those which specifically bind SP.

Antibodies to SP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with SP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to SP have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of SP amino acids may be fused with those of another protein such as keyhole limpet hemocyanin and antibody produced against the chimeric molecule.

Monoclonal antibodies to SP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M.S. et al. (1984) Nature 312:604–608; Takeda, S. et al. (1985) Nature 314:452–454). Alternatively, techniques described for the production of single chain antibodies may be adapted, using methods known in the art, to produce SP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for SP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between SP and its specific antibody. A two-site, monoclonal-based immunoassay utilizing monoclonal antibodies reactive to two non-interfering SP epitopes is preferred, but a competitive binding assay may also be employed (Maddox, supra).

In another embodiment of the invention, the polynucleotides encoding SP, or any fragment or complement thereof, may be used for therapeutic purposes. In one aspect, the complement of the polynucleotide encoding SP may be used in situations in which it would be desirable to block the transcription of the mRNA. In particular, cells may be transformed with sequences complementary to polynucleotides encoding SP. Thus, complementary molecules or fragments may be used to modulate SP activity, or to achieve regulation of gene function. Such technology is now well known in the art, and sense or antisense oligonucleotides or larger fragments, can be designed from various locations along the coding or control regions of sequences encoding SP.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding SP. These techniques are described both in Sambrook et al. (supra) and in Ausubel et al. (supra).

Genes encoding SP can be turned off by transforming a cell or tissue with expression vectors which express high levels of a polynucleotide or fragment thereof which encodes SP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding SP (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding SP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding SP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of SP, antibodies to SP, mimetics, agonists, antagonists, or inhibitors of SP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmnaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of SP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example SP or fragments thereof, antibodies of SP, agonists, antagonists or inhibitors of SP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind SP may be used for the diagnosis of conditions or diseases characterized by expression of SP, or in assays to monitor patients being treated with SP, agonists, antagonists or inhibitors. The antibodies useful for diagnostic purposes may be prepared in the same manner as those described above for therapeutics. Diagnostic assays for SP include methods which utilize the antibody and a label to detect SP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring SP are known in the art and provide a basis for diagnosing altered or abnormal levels of SP expression. Normal or standard values for SP expression are established by combining body fluids or cell extracts taken from normal mammalian subjects, preferably human, with antibody to SP under conditions suitable for complex formation. The amount of standard complex formation may be quantified by various methods, but preferably by photometric means. Quantities of SP expressed in subject, control, and disease, samples from biopsied tissues are compared with the standard values. Deviation between standard and subject values establishes the parameters for diagnosing disease.

In another embodiment of the invention, the polynucleotides encoding SP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of SP may be correlated with disease. The diagnostic assay may be used to distinguish between absence, presence, and excess expression of SP, and to monitor regulation of SP levels during therapeutic intervention.

In one aspect, hybridization with PCR probes which are capable of detecting polynucleotide sequences, including genomic sequences, encoding SP or closely related molecules, may be used to identify nucleic acid sequences which encode SP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding SP, alleles, or related sequences.

Probes may also be used for the detection of related sequences, and should preferably contain at least 50% of the nucleotides from any of the SP encoding sequences. The hybridization probes of the subject invention may be DNA or RNA and derived from the nucleotide sequence of SEQ ID NOs:1–15 and 17, or fragments encompassing the nucleic acid sequence $A_{24}$ to $G_{44}$, $G_{159}$ to $C_{182}$, $G_{561}$ to $A_{596}$, or $A_{1011}$ to $T_{1046}$ of SEQ ID NO:17, or from genomic sequences including promoter, enhancer elements, and introns of the naturally occurring SP.

Means for producing specific hybridization probes for DNAs encoding SP include the cloning of nucleic acid sequences encoding SP or SP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding SP may be used for the diagnosis of conditions, disorders, or diseases which are associated with either increased or decreased expression of SP. Examples of such conditions, disorders or diseases include cancers such as adenocarcinoma, leukemia, lymphoma, melanoma, myeloma, sarcoma, teratocarcinoma, and cancers of the adrenal gland, bladder, bone, brain, breast, cervix, gall bladder, ganglia, gastrointestinal tract, heart, kidney, liver, lung, bone marrow, muscle, ovary, pancreas, parathyroid, penis, prostate, salivary glands, skin, spleen, testis, thymus, thyroid, and uterus; neuronal disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder; and immune response associated with disorders such as AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and thyroiditis. The polynucleotide sequences encoding SP may be used in Southern or northern analysis, dot blot, or other membrane-based technologies; in PCR technologies; or in dipstick, pin, ELISA assays or microarrays utilizing fluids or tissues from patient biopsies to detect altered SP expression. Such qualitative or quantitative methods are well known in the art.

In a particular aspect, the nucleotide sequences encoding SP may be useful in assays that detect activation or induction of various cancers, particularly those mentioned above. The nucleotide sequences encoding SP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding SP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of SP, a normal or standard profile for expression is established. This may be accomplished by combining body fluids or cell extracts taken from normal subjects, either animal or human, with a sequence, or a fragment thereof, which encodes SP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding SP may involve the use of PCR. Such oligomers may be chemically synthesized, generated enzymatically, or produced in vitro. Oligomers will preferably consist of two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of SP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents.

In one embodiment, the microarray is prepared and used according to the methods known in the art such as those described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619).

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably about 15 to 30 nucleotides in length, and most preferably about 20 to 25 nucleotides in length. For a certain type of microarray, it may be preferable to use oligonucleotides which are only 7 to 10 nucleotides in length. The microarray may contain oligonucleotides which cover the known 5' (or 3') sequence, or may contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from 2 to 1,000,000.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or any other type of membrane, filter, chip, glass slide, or any other suitable solid support.

In one aspect, the oligonucleotides may be synthesized on the surface of the substrate by using a chemical coupling procedure and an ink jet application apparatus, such as that described in PCT application WO95/251116 (Baldeschweiler et al.). In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including multichannel pipettors or robotic instruments; Brinkmann, Westbury, N.Y.) and may contain 8, 24, 96, 384, 1536 or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and oligolabeling kits (Amersham Pharmacia Biotech) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or finctional analysis of the sequences, mutations, variants, or polymorphisms among samples (Heller, R. A. et al., (1997) Proc. Natl. Acad. Sci. 94:2150–55).

In another embodiment of the invention, the nucleic acid sequences which encode SP may be used to generate hybridization probes which are useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions or single chromosome cDNA libraries (cf. Price, C. M. (1993) Blood Rev. 7:127–134; Trask, B. J. (1991) Trends Genet. 7:149–154).

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding SP on a physical chromosomal map and a specific disease, or predisposition to a specific disease, may help delimit the region of DNA associated with that disease. The nucleotide sequences of the subject invention may be used to detect differences in gene sequences between normal, carrier, and affected individuals.

In situ hybridization of chromosomal preparations and physical mapping techniques, linkage analysis using established chromosomal markers, may be used to extend genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, and affected individuals.

In another embodiment of the invention, SP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between SP and the agent being tested, may be measured.

Another technique for drug screening which may be used provides for high throughput screening of compounds having suitable binding affinity to the protein of interest as described in published PCT application WO84/03564. In this method, as applied to SP large numbers of different small test compounds are synthesized on a solid substrate, such as plastic pins or some other surface. The test compounds are reacted with SP, or fragments thereof, and washed. Bound SP is then detected by methods well known in the art. Purified SP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding SP specifically compete with a test compound for binding SP. In this manner, the antibodies can be used to detect the presence of any peptide which shares one or more antigenic determinants with SP.

In additional embodiments, the nucleotide sequences which encode SP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the UTRSNOT11 cDNA library, from which Incyte Clone 2547002 was isolated, is described. Preparation and sequencing of cDNAs in libraries in the LIFESEQ database (Incyte Pharmaceuticals, Palo Alto, Calif.) have varied over time, and the gradual changes involved use of kits, plasmids, and machinery available at the particular time the library was made and analyzed.

I UTRSNOT011 cDNA Library Construction

The UTRSNOT11 cDNA library was constructed from microscopically normal uterine tissue obtained from a 43-year-old female during a vaginal hysterectomy following the diagnosis of uterine leiomyoma. Pathology indicated that the myometrium contained an intramural leiomyoma and a submucosal leiomyoma. The endometrium was proliferative, however, the cervix and fallopian tubes were unremarkable. The right and left ovaries contained corpus lutea. The patient presented with metrorrhagia and deficiency anemia. Patient history included benign hypertension and atherosclerosis. Medications included Provera® tablets (medroxyprogesterone acetate; The Upjohn Company, Kalamazoo, Mich.), iron and vitamins. Family history included benign hypertension in the father, atherosclerosis in a grandparent, malignant colon neoplasms in the mother, father, and a grandparent.

For the UTRSNOT11 library, the frozen tissue was homogenized and lysed in Trizol reagent (1 gm tissue/10 ml Trizol; Cat. #10296–028; Life Technologies), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and treated with DNase for 25 min at 37° C. The RNA was re-extracted three times with acid phenol-chloroform pH 4.7 and precipitated using 0.3M sodium acetate and 2.5 volumes ethanol. The mRNA was isolated with the OLIGOTEX kit (QIAGEN, Inc., Chatsworth, Calif.) and used to construct the cDNA library.

The mRNA was handled according to the recommended protocols in the SUPERSCRIPT Plasmid System for cDNA Synthesis and Plasmid Cloning (Cat. #18248–013, Life Technologies). The cDNAs were fractionated on a SEPHAROSE CL4B column (Cat. #275105–01; Amersham Pharmacia Biotech), and those cDNAs exceeding 400 bp were ligated into pINCY 1 (Incyte Pharmaceuticals). The plasmid pINCY 1 was subsequently transformed into DH5α competent cells (Cat. #18258–012; Life Technologies).

II Isolation and Sequencing of cDNA Clones

Plasmid DNA was released from the cells and purified using the REAL Prep 96 plasmid kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger, et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques use BLAST to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding SP occurs. Abundance and percent abundance are also reported. Abundance directly reflects the number of times a particular transcript is represented in a cDNA library, and percent abundance is abundance divided by the total number of sequences examined in the cDNA library.

V Extension of SP Encoding Polynucleotides

The nucleic acid sequence of one of the nucleotide sequences of the present invention was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Life Technologies) were used to extend the sequence. If more than one extension was necessary or desired, additional sets of primers were designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK kit (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of one of the nucleotide sequences of the present invention were used to obtain 5' regulatory sequences using the procedure above, oligonucleotides designed for 5' extension, and an appropriate genomic library.

VI Labeling and Use of Individual Hybridization Probes

Hybridization probes derived from one of the nucleotide sequences of the present invention are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham Pharmacia Biotech) and T4 polynucleotide kinase (DuPont NEN, Boston, Mass.). The labeled oligonucleotides are substantially purified with SEPHADEX G-25 superfine resin column (Amersham Pharmacia Biotech). An aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, one of the nucleotide sequences of the present invention are examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20 mers are synthesized and arranged on the surface of the silicon chip using a light-directed chemical process, such as that discussed in Chee, supra.

In the alternative, a chemical coupling procedure and an ink jet device are used to synthesize oligomers on the surface of a substrate (cf. Baldeschweiler, supra). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequence complementary to the sequence encoding SP, or any part thereof, is used to detect, decrease, or inhibit expression of naturally occurring SP. Although use of oligonucleotides comprising from about 15 to about 30 basepairs is described, essentially the same procedure is used with smaller or larger sequence fragments. Appropriate oligonucleotides are designed using OLIGO 4.06 software and the coding sequence of one of the nucleotide sequences of the present invention. To inhibit transcription, a complementary oligonucleotide is designed from the most unique 5' sequence and used to prevent promoter binding to the coding sequence. To inhibit translation, a complementary oligonucleotide is designed to prevent ribosomal binding to the transcript encoding SP.

IX Expression of SP

Expression of SP is accomplished by subcloning the cDNAs into appropriate vectors and transforming the vectors into host cells. In this case, the cloning vector is also used to express SP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of SP into the bacterial growth media which can be used directly in the following assay for activity.

X Demonstration of SP Activity

Cell proliferation SP may be expressed in a mammalian cell line such as DLD-1 or HCT116 (ATCC; Bethesda, Md.) by transforming the cells with a eukaryotic expression vector encoding SP. Eukaryotic expression vectors are commercially available and the techniques to introduce them into cells are well known to those skilled in the art. The effect of SP on cell morphology may be visualized by microscopy; the effect on cell growth may be determined by measuring cell doubling-time; and the effect on tumorigenicity may be assessed by the ability of transformed cells to grow in a soft agar growth assay (Groden, J. et al. (1995) Cancer Res. 55:1531–1539).

Receptor Sp such as those encoded by SEQ ID NOs:17, 15, 12, 6 and 1 may be expressed in heterologous expression systems and their biological activity tested utilizing the purinergic receptor system ($P_{2U}$) as published by Erb, et al. (1993; Proc. Natl. Acad. Sci. 90:10449–53). Because cultured K562 human leukemia cells lack $P_{2U}$ receptors, they can be transfected with expression vectors containing either normal or chimeric $P_{2U}$ and loaded with fura-a, fluorescent probe for $Ca^{++}$. Activation of properly assembled and functional extracellular SP-transmembrane/intracellular $P_{2U}$ receptors with extracellular UTP or ATP mobilizes intracellular $Ca^{++}$ which reacts with fura-a and is measured spectrofluorometrically. Bathing the transfected K562 cells in microwells containing appropriate ligands will trigger binding and fluorescent activity defining effectors of SP. Once ligand and function are established, the $P_{2U}$ system is useful for defining antagonists or inhibitors which block binding and prevent such fluorescent reactions.

XI Production of SP Specific Antibodies

SP that is substantially purified using PAGE electrophoresis (Sambrook, supra), or other purification techniques, is used to immunize rabbits and to produce antibodies using standard protocols. The amino acid sequence deduced from one of the nucleotide sequences of the present invention is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring SP Using Specific Antibodies

Naturally occurring or recombinant SP is substantially purified by immunoaffinity chromatography using antibodies specific for SP. An immunoaffinity column is constructed by covalently coupling SP antibody to an activated chromatographic resin, such as CNBr-activated SEPHAROSE (Amersham Pharmacia Biotech). After the coupling, the resin is blocked and washed according to the manufacturer's instructions.

Media containing SP is passed over the immunoaffinity column, and the column is washed under conditions that allow the preferential absorbance of SP (e.g., high ionic strength buffers in the presence of detergent). The column is eluted under conditions that disrupt antibody/protein binding (eg, a buffer of pH 2–3 or a high concentration of a chaotrope, such as urea or thiocyanate ion), and SP is collected.

XIII Identification of Molecules Which Interact with SP

SP or biologically active fragments thereof are labeled with $^{125}I$ Bolton-Hunter reagent (Bolton et al. (1973) Biochem. J. 133: 529). Candidate molecules previously arrayed in the wells of a multi-well plate are incubated with the labeled SP, washed and any wells with labeled SP complex are assayed. Data obtained using different concentrations of SP are used to calculate values for the number, affinity, and association of SP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence having a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:17.

2. A microarray containing at least a fragment of at least one of the polynucleotides encoding signal peptide-containing proteins of claim 1.

3. A fragment of claim 2 wherein said fragment comprises the nucleic acid sequence of SEO ID NO:17 extending from $A_{24}$ to $G_{44}$, $G_{159}$ to $C_{182}$, $G_{561}$ to $A_{596}$, or $A_{1011}$ to $T_{1046}$.

4. An isolated and purified polynucleotide having a nucleic acid sequence which is complementary to the nucleic acid sequence of the polynucleotide of claim 1.

5. A composition comprising the polynucleotide of claim 1.

6. A composition comprising the polynucleotide sequence of claim 1.

7. An expression vector containing the polynucleotide of claim 1.

8. A host cell containing the vector of claim 7.

9. A method for producing a polypeptide encoding a signal peptide-containing protein, the method comprising the steps of:

a) culturing the host cell of claim 8 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
            (A) LENGTH: 619 base pairs
            (B) TYPE: nucleic acid
            (C) STRANDEDNESS: single
            (D) TOPOLOGY: linear (vii) IMMEDIATE SOURCE:
            (A) LIBRARY: NEUTGMT01
            (B) CLONE: 1221102

(xi) SEQUENCE DESCRIPTION: SEQ ID NO:1:

```
GGACAATGAA CATTGTCCCT CGGACAAAAG TGAAAACTAT CAAGATGTTC CTCATTTTAA      60
ATCTGTTGTT TTTGCTCTCC TGGCTGCCTT TTCATGTAGC TCAGCTATGG CACCCCCATG     120
AACAAGACTA TAAGAAAAGT TCCCTTGTTT TCACAGCTAT CACATGGATA TCCTTTAGTT     180
CTTCAGCCTC TAAACCTACT CTGTATTCAA TTTATAATGC CAATTTCGGA GAGGGATGAA     240
AGAGACTTTT TGCATGTCCT CTATGAAATG TTACCGAAGC AATGCCTATA CTATCACAAC     300
AAGTTCAAGG ATGGCCAAAA AAAACTACGT TGGCATTTCA GAAATCCCTT CCATGGCCAA     360
AACTATTACC CAAAGACTCG ATCTATGACT CATTTGACAG AGAAGCCAAG GAAAAAAAGC     420
TTGCTTGGCC CATTAACTCA AATCCACCAA ATACTTTTGT CCAAGTTCTC ATTCTTTCAA     480
TTGTTATGCA CCAGAGATTA AAAAGCTTTA ACTATAAAAA CAGAAGCTAT TTACATATTT     540
GTTTTCACTC AACTTTCCAA GGGAAATGTT TTATTTTGTA AAATGCATTC ATTTGTTTAC     600
TGTAAAAAAA AAAAAAAA                                                  619
```

(2) INFORMATION FOR SEQ ID NO:2:

(i) SEQUENCE CHARACTERISTICS:
            (A) LENGTH: 742 base pairs
            (B) TYPE: nucleic acid
            (C) STRANDEDNESS: single
            (D) TOPOLOGY: linear (vii) IMMEDIATE SOURCE:
            (A) LIBRARY: COLNFET02
            (B) CLONE: 1457779

(xi) SEQUENCE DESCRIPTION: SEQ ID NO:2:

```
CCTGGAGCCA GGTGCACAGC GCATCGCCCG AGGCTGTCAC CGCCCTGCCC CGCCCACCCC      60
AGCTGTCCTG GACCCAGGGG CAGGGAGAGG CTGGACGCCA GGTGCGCGGA CACAGAAGCG     120
TCTAAGCACA GCTTCCTCCT TGCCGCTCCG GGAAGTGGGC AGCCAGCCCA GGAACCAGTA     180
CCACCTGCAC CATGGGGCTG TCCCGGAAGG AGCAGGTCTT CTTGGCCCTG CTGGGGGCCT     240
CGGGGGTCTC AGGCCTCACG GCACTCATTC TCCTCCTGGT GGAGGCCACC AGCGTGCTCC     300
TGCCCACAGA CATCAAGTTT GGGATCGTGT TTGATGCGGG CTCCTCCCAC ACGTCCCTCT     360
TCCTGTATCA GTGGCCGGCG AACAAGGAGA ATGCACGGG TGTGGTCAGC CAGGCCCTGG     420
CCTGCCAGGT GGAAGGGCCT GGAATCTCCT CCTACACTTC TAATGCTGCA CAGGCTGGTG     480
AGAGCCTGCA GGGCTGCTTG GAGGAGGCGC TGGTGCTGAT CCCAGAGGCC CAGCATCGGA     540
AAACACCCAC GTTCCTGGGG GCCACGGCTG GCATGAGGTT GCTCAGCCGG AAGAACAGCT     600
CTCAGGGCCA GGGACATCTT TGCAGCAGTC ACCCAGGTCC TGGGGCCGGT CTCCCGTGGA     660
```

```
CTTTTGGGGT GCCGAGCTCC TGGCCGGGCA GGCCGAAGTG GCCTTTGGTT GGATCACTGT      720

CAACTACGGC TTGGGGACGT TT                                               742

(2) INFORMATION FOR SEQ ID NO:3:

(i) SEQUENCE CHARACTERISTICS:
        (A) LENGTH: 1141 base pairs
        (B) TYPE: nucleic acid
        (C) STRANDEDNESS: single
        (D) TOPOLOGY: linear (vii) IMMEDIATE SOURCE:
        (A) LIBRARY: PROSNOT15
        (B) CLONE: 1682433

(xi) SEQUENCE DESCRIPTION: SEQ ID NO:3:

CGCTGAAACC CTGGGCGGCG GCAAGCTGTG CGACCTCTTC TGCGGCCGGC CTGGGCAGGT       60

GTCTTCCTCG AGAGGCAGGC AGGGGATCCC GGACCCTTAT ACAGGATGCT GTGTTCTTTG      120

CTCCTTTGTG AATGTCTGTT GCTGGTAGCT GGTTATGCTC ATGATGATGA CTGGATTGAC      180

CCCACAGACA TGCTTAACTA TGATGCTGCT TCAGGAACAA TGAGAAAATC TCAGGCAAAA      240

TATGGTATTT CAGGGGAAAA GGATGTCAGT CCTGACTTGT CATGTGCTGA TGAAATATCA      300

GAATGTTATC ACAAACTTGA TTCTTTAACT TATAAGATTG ATGAGTGTGA AAAGAAAAAG      360

AGGGAAGACT ATGAAAGTCA AGCAATCCT GTTTTTAGGA GATACTTAAA TAAGATTTTA       420

ATTGAAGCTG GAAAGCTTGG ACTTCCTGAT GAAAACAAAG GCGATATGCA TTATGATGCT      480

GAGATTATCC TTAAAAGAGA AACTTTGTTA GAAATACAGA AGTTTCTCAA TGGAGAAGAC      540

TGGAAACCAG GTGCCTTGGA TGATGCACTA AGTGATATTT TAATTAATTT TAAGTTTCAT      600

GATTTTGAAA CATGGAAGTG GCGATTCGAA GATTCCTTTG GAGTGGATCC ATATAATGTG      660

TTAATGGTAC TTCTTTGTCT GCTCTGCATC GTGGTTTTAG TGGCTACCGA GCTGTGGACA      720

TATGTACGTT GGTACACTCA GTTGAGACGT GTTTTAATCA TCAGCTTTCT GTTCAGTTTG      780

GGATGGAATT GGATGTATTT ATATAAGCTA GCTTTTGCAC AGCATCAGGC TGAAGTCGCC      840

AAGATGGAGC CATTAAACAA TGTGTGTGCC AAAAAGATGG ACTGGACTGG AAGTATCTGG      900

GAATGGTTTA GAAGTTCATG GACCTATAAG GATGACCCAT GCCAAAAATA CTATGAGCTC      960

TTACTAGTCA ACCCTATTTG GTTGGTCCCA CCAACAAAGG CACTTGCAGT TACATTCACC     1020

ACATTTGTAA CGGAGCCATT GAAGCATATT GGAAAAGGAA CTGGGGAATT TATTAAAGCA     1080

CTCATGAAGG AAATTCCAGC GCTGCTTCAT CTTCCAGTGC TGATAATTAT GGCATTAGCC     1140

A                                                                    1141

(2) INFORMATION FOR SEQ ID NO:4:

(i) SEQUENCE CHARACTERISTICS:
        (A) LENGTH: 898 base pairs
        (B) TYPE: nucleic acid
        (C) STRANDEDNESS: single
        (D) TOPOLOGY: linear (vii) IMMEDIATE SOURCE:
        (A) LIBRARY: BLADTUT06
        (B) CLONE: 1899132

(xi) SEQUENCE DESCRIPTION: SEQ ID NO:4:

TGCGAACCTG GCCCGTGCGG AAAGGGCGCG GAGAGCCCCG GCGCGGAGCA GGCGGGGGAC       60

GGTATTCAGA ATTCGAGCGC AGGAGCTCCG CTTCTCCACC TGCTCCCGGG GAGCTATTGG      120

GATCCAGAGA ATCACCCGCT GATGGTTTTT GCCCAGGCCT GAAACAACCA GAGAGCTACG      180
```

```
GGAAAGGAAG GGCTTGGCTT GCCAGAGGAA TTTTCCAAGT GCTCAAACGC CAGGCTTACG    240

GCGCCTGTGA TCCGTCCAGG AGGACAAAGT GGGATTTGAA GATCCACTCC ACTTCTGCTC    300

ATGGCGGGCC AGGGCCTGCC CCTGCACGTG GCCACACTGC TGACTGGGCT GCTGGAATGC    360

CTGGGCTTTG CTGGCGTCCT CTTTGGCTGG CCTTCACTAG TGTTTGTCTT CAAGAATGAA    420

GATTACTTTA AGGATCTGTG TGGACCAGAT GCTGGGCCGA TTGGCAATGC CACAGGGCAG    480

GCTGACTGCA AAGCCCAGGA TGAGAGGTTC TCACTCATCT TCACCCTGGG GTCCTTCATG    540

AACAACTTCA TGACATTCCC CACTGGCTAC ATCTTTGACC GGTTCAAGAC CACCGTGGCA    600

CGCCTCATAG CCATATTTTT CTACACCACC GCCACACTCA TCATAGCCTT CACCTCTGCA    660

GGCTCAGCCG TGCTGCTCTT CCTGGCCATG CCAATGCTCA CCATTGGGGG AATCCTGTTT    720

CTCATCACCA ACCTGCAGAT TGGGAACCTA TTTGGCCAAC ACCGTTCGAC CATCATCACT    780

CTGTACAATG GAGCATTTGA CTCTTCCTCG GCAGTCTTCC TTATTATTAA GCTTCTTTAT    840

GAAAAAGGCA TCAGCCTCAG GGCCTGCACC TGGCGCCTCG AGCACGACTA TATATTGC     898

(2) INFORMATION FOR SEQ ID NO:5:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (vii) IMMEDIATE SOURCE:
        (A) LIBRARY: CONNTUT01
        (B) CLONE: 1907344

(xi) SEQUENCE DESCRIPTION: SEQ ID NO:5:

GCTCAGCTGT GGGCTTAGGA AGCAGAGCCT GGGGCATCTC CACCATGGCC TGGACCCCTC     60

TCCTCCTCCA GCTTCTCACC CTCTGCTCAG GGTCCTGGGC ACAGTCTGCG CTGACCCAGG    120

AAGCCTCGGT GTCAGGGACC GTGGGACAGA AGGTCACCCT GTCCTGTTCT GGAAACAACA    180

ACAACATTGG AAGTTATGCT GTGGGCTGGT ACCAACAGAT TTCTCACGGT GTTCTCAAAA    240

CTGTGATATT TGGAAATTCT CCGCCCTCAG GGATCCCTTA CCGCTTCTCT GGCTCAAAGT    300

CTGGGACCAC AGCCTCCCTG ACTATCTCGG GCCTCCAGCC TGAGGACGAG GCTGATTATT    360

ATTTTTCAAC ATGGGACTAC AGACTCAGTG CTGTGGTTTT CGGCGGAAGG ACCAAACTGA    420

CCGTCCTAGG TCAGCCCAAG GCTGCCCCCT                                    450

(2) INFORMATION FOR SEQ ID NO:6:

(i) SEQUENCE CHARACTERISTICS:
        (A) LENGTH: 2111 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT04
        (B) CLONE: 1963651

(xi) SEQUENCE DESCRIPTION: SEQ ID NO:6:

AAGTGCTCAG CACTAAGGGA GCCAGCGCAC AGCACAGCCA GGAAGGCGAG CGAGCCCAGC     60

CAGCCCAGCC AGCCCAGCCA GCCCGGAGGT ATCTGTGAGA TAGGTGCTGC TGTCCTGGGG    120

AGGTAGATGC AGACAGATTA ACTCTCAAGG TCATTTGATT GCCCGCCTCA GAACGATGGA    180

TCTGCATCTC TTCGACTACT CAGAGCCAGG GAACTTCTCG GACATCAGCT GGCCATGCAA    240

CAGCAGCGAC TGCATCGTGG TGGACACGGT GATGTGTCCC AACATGCCCA ACAAAAGCGT    300
```

```
CCTGCTCTAC ACGCTCTCCT TCATTTACAT TTTCATCTTC GTCATCGGCA TGATTGCCAA      360

CTCCGTGGTG GTCTGGGTGA ATATCCAGGC CAAGACCACA GGCTATGACA CGCACTGCTA      420

CATCTTGAAC CTGGCCATTG CCGACCTGTG GGTTGTCCTC ACCATYCCAG TCTGGGTGGT      480

CAGTCTCGTG GMAGCACAAC CAGTGGCCCA TGGGCGAGCT CACGTGCAAA GTCACACACC      540

TCATCTTYTC CATCAACCTC TTCGGCAGCA TTTTCTTCCT CACGTGCATG AGCGTGGACC      600

GCTACCTCTC CATCACCTAC TTCACCAACA CCCCCAGCAG CAGGAAGAAG ATGGTACGCC      660

GTGTCGTCTG CATCCTGGTG TGGCTGCTGG CCTTCTGCGT GTCTCTGCCT GACACCTACT      720

ACCTGAAGAC CGTCACGTCT GCGTCCAACA ATGAGACCTA CTGCCGGTCC TTCTACCCCG      780

AGCACAGCAT CAAGGAGTGG CTGATCGGCA TGGAGCTGGT CTCCGTTGTC TTGGGCTTTG      840

CCGTTCCCTT CTCCATTATC GCTGTCTTCT ACTTCCTGCT GGCCAGAGCC ATCTCGGCGT      900

CCAGTGACCA GGAGAAGCAC AGCAGCCGGA AGATCATCTT CTCCTACGTG GTGGTCTTCC      960

TTGTCTGCTG GTTGCCCTAC CACGTGGCGG TGCTGCTGGA CATCTTCTCC ATCCTGCACT     1020

ACATCCCTTT CACCTGCCGG CTGGAGCACG CCCTCTTCAC GGCCCTGCAT GTCACACAGT     1080

GCCTGTCGCT GGTGCACTGC TGCGTCAACC CTGTCCTCTA CAGCTTCATC AATCGCAACT     1140

ACAGGTACGA GCTGATGAAG GCCTTCATCT TCAAGTACTC GGCCAAAACA GGGCTCACCA     1200

AGCTCATCGA TGCCTCCAGA GTCTCAGAGA CGGAGTACTC TGCCTTGGAG CAGAGCACCA     1260

AATGATCTGC CCTGGAGAGG CTCTGGGACG GGTTTACTTG TTTTTGAACA GGGTGATGGG     1320

CCCTATGGTT TTCTAGRGCA AAGCAAAGYM SCYYCGGGGA AYCYYRATCC CCCSCTTGAG     1380

TCCMSMGTGA AGAGGGGAGS ACGTGCCCCA GCTTGGCATC CAWTCTCTCT TGGKCTCTTG     1440

ATGACGCAGC TGTCATTTGG CTGTAARCAA GTGCTGACAG TTTTSCAACR GGGCAGAGCT     1500

GTTGTCSCAC AGCCAGTGCC TGTGCCGTCA GAGCCCAGCT GAGGACMGGC TTGCCCKGGA     1560

CCTYCTGAWA AGATAGGATT TYCKGKGTTY CCKGAATTTT TWAWATGGKG ATTKGTATTT     1620

AAAWTTTAAG ACCTTWATTT YCYCACTATT GGKGKACCTT ATAAATGTAT TKGAAAGTTA     1680

AATATATTTT AAATATTGTT TGGGAGGCAT AGTGCTGACA TATATTCAGA GTGTTGTAGT     1740

TTTAAGGTTA GCGTGACTTC AGTTTTGACT AAGGATGACA CTAATTGTTA GCTGTTTTGA     1800

AATTATATAT ATATAAATAT ATATAAATAT ATAAATATAT GCCAGTCTTG GCTGAAATGT     1860

TTTATTTACC ATAGTTTTAT ATCTGTGTGG TGTTTTGTAC CGGCACGGGA TATGGAACGA     1920

AAACTGCTTT GTAATGCAGT TTGTGACATT AATAGTATTG TAAAGTTACA TTTTAAAATA     1980

AACAAAAAAC TGTTCTGGAC TGCAAATCTG CACACACAAC GAACAGTTGC ATTTCAGAGA     2040

GTTCTCTCAA TTTGTAAGTT ATTTTTTTTT AATAAAGATT TTTGTTTCCT AAAAATGCAA     2100

AAAAAAAAA A                                                         2111
```

(2) INFORMATION FOR SEQ ID NO:7:

(i) SEQUENCE CHARACTERISTICS:
        (A) LENGTH: 700 base pairs
        (B) TYPE: nucleic acid
        (C) STRANDEDNESS: single
        (D) TOPOLOGY: linear (vii) IMMEDIATE SOURCE:
        (A) LIBRARY: PANCTUT02
        (B) CLONE: 1976095

(xi) SEQUENCE DESCRIPTION: SEQ ID NO:7:

```
GACGCCAGCG CCTGCAGAGG NTGAGCAGGG AAAAAGCCAG TGCCCAGCG GAAGACNAGC       60
```

```
TCAGAGCTGG TCTGCCATGG ACATCCTGGT CCCACTCCTG CAGCTGCTGG TGCTGCTTCT      120

TACCCTGCCC CTGCACCTCA TGGCTCTGCT GGGCTGCTGG CAGCCCCTGT GCAAAAGCTA      180

CTTCCCCTAC CTGATGGCCG TGCTGACTCC CAAGAGCAAC CGCAAGATGG AGAGCAAGAA      240

ACGGGAGCTC TTCAGCCAGA TAAAGGGGCT TACAGGAGCC TCCGGGAAAG TGGCCCTACT      300

GGAGCTGGGC TGCGGAACCG GAGCCAACTT TCAGTTCTAC CCACCGGGCT GCAGGGTCAC      360

CTGCCTAGAC CCAAATCCCC ACTTTGAGAA GTTCCTGACA AAGAGCATGG CTGAGAACAG      420

GCACCTCCAA TATGAGCGGT TTGTGGTGGC TCCTGGAGAG GACATGAGAC AGCTGGCTGA      480

TGGCTCCATG GATGTGGTGG TCTGCACTCT GGTGCTGTGC TCTGTGCAGA GCCCAAGGAA      540

GGTCCTGCAG GAGGTCCGGA GAGTACTGAG ACCGGGAGGT GTGCTCTTTT TCTGGGAGCA      600

TGTGGCAGAA CCATATGGAA GCTGGGCCTT CATGTGGCAG CAAGTTTTCG AGCCCACCTG      660

GAAACACATT GGGGATGGCT TGCTGCCTCA CCAGAGAGAC                            700

(2) INFORMATION FOR SEQ ID NO:8:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (vii) IMMEDIATE SOURCE:
        (A) LIBRARY: HNT3AZT01
        (B) CLONE: 2417676

(xi) SEQUENCE DESCRIPTION: SEQ ID NO:8:

GGGAATTTCC CTTATCTCCT TCGCAGTGCA GCTCCTTCAA CCTCGCCATG GCCTCTGCCG       60

GAATGCAGAT CCTGGGAGTC GTCCTGACAC TGCTGGGCTG GGTGAATGGC CTGGTCTCCT      120

GTGCCCTGCC CATGTGGAAG GTGACCGCTT TCATCGGCAA CAGCATCGTG GTGGCCCAGG      180

TGGTGTGGGA GGGCCTGTGG ATGTCCTGCG TGGTGCAGAG CACCGGCCAG ATGCAGTGCA      240

AGGTGTACGA CTCACTGCTG GCGCTGCCAC AGGACCTGCA GGCTGCACGT GCCCTCTGTG      300

TCATCGCCCT CCTTGTGGCC CTGTTCGGCN TGCTGGTCTA CCTTGCTGGG GCCAAGTTTA      360

CCA                                                                   363

(2) INFORMATION FOR SEQ ID NO:9:

(i) SEQUENCE CHARACTERISTICS:
        (A) LENGTH: 575 base pairs
        (B) TYPE: nucleic acid
        (C) STRANDEDNESS: single
        (D) TOPOLOGY: linear (vii) IMMEDIATE SOURCE:
        (A) LIBRARY: SINTNOT13
        (B) CLONE: 1805538

(xi) SEQUENCE DESCRIPTION: SEQ ID NO:9:

CNGNTCGAGG CTAAGAGGAC AGGATGAGGC CCGGCCTCTC ATTTCTCCTA GCCCTTCTGT       60

TCTTCCTTGG CCAAGCTGCA GGGGATTTGG GGATGTGGG ACCTCCAATT CCCAGCCCCG       120

GCTTCAGCTC TTTCCCAGGT GTTGACTCCA GCTCCAGCTT CAGCTCCAGC TCCAGGTCGG      180

GCTCCAGCTC CAGCCGCAGC TTAGGCAGCG GAGGTTCTGT GTCCCAGTTG TTTTCCAATT      240

TCACCGGCTC CGTGGATGAC CGTGGGACCT GCCAGTGCTC TGTTTCCCTG CCAGACACCA      300

CCTTTCCCGT GGACAGAGTG GAACGCTTGG AATTCACAGC TCATGTTCTT TCTCAGAAGT      360

TTGAGAAAGA ACTTTCCAAA GTGAGGGAAT ATGTCCAATT AATTAGTGTG TATGAAAAGA      420
```

```
AACTGTTAAA CCTAATGTCC GAATTGACAT CATGGAGAAG GATACCATTT CTTACACTGA      480

ACTGGACTTC GAGCTGATCA AGGTAGAAGT GAAGGAGATG GAAAAACTGG TCATACAGCT      540

GAAGGAGAGT TTGGTGGAAG TCAGAAATTG TTGAC                                 575
```

(2) INFORMATION FOR SEQ ID NO:10:

(i) SEQUENCE CHARACTERISTICS:
        (A) LENGTH: 1637 base pairs
        (B) TYPE: nucleic acid
        (C) STRANDEDNESS: single
        (D) TOPOLOGY: linear (vii) IMMEDIATE SOURCE:
        (A) LIBRARY: SKINBIT01
        (B) CLONE: 1869688

(xi) SEQUENCE DESCRIPTION: SEQ ID NO:10:

```
ACNCAGCCTT TTNCCCGATT CNCCCTTTCC TGCCTTCGGT TTCNTCCCAA TTCTTACCCA       60

TCCCCTACNA GCTGCCATCC CTGACACCCT TCTCTCCTGG GCCACGCAGT CCAACCTGAA      120

CGGGAGCGGG GAGGTATCCT GGCACCTTCC TTGGCTCTTA CNCCTCGGTT TCTCACAGCG      180

GGGCCGGCGC CGCCATGGCG GCCGTGTTTG ATTTGGATTT GGAGACGGAG GAAGGCAGCG      240

AGGGCGAGGG CGAGCCAGAG CTCAGCCCCG CGGACGCATG TCCCCTTGCC GAGTTGAGGG      300

CAGCTGGCCT AGAGCCTGTG GGACACTATG AAGAGGTGGA GCTGACTGAG ACCAGCGTGA      360

ACGTTGGCCC AGAGCGCATC GGGCCCCACT GCTTTGAGCT GCTGCGTGTG CTGGGCAAGG      420

GGGGCTATGG CAAGGTGTTC CAGGTGCGAA AGGTGCAAGG CACCAACTTG GGCAAAATAT      480

ATGCCATGAA AGTCCTAAGG AAGGCCAAAA TTGTGCGCAA TGCCAAGGAC ACAGCACACA      540

CACGGGCTGA GCGGAACATT CTAGAGTCAG TGAAGCACCC CTTTATTGTG GAACTGGCCT      600

ATGCCTTCCA GACTGGTGGC AAACTCTACC TCATCCTTGG ATTGCCTCAG TGGTGGCGAG      660

CTCTTCACGC ATCGGAGCG AGAGGGCATC TTCCTGGAAG ATACGGCCTG CTTCTACCTG       720

GCTGAGATCA CGCTGGCCCT GGGCCATCTC CACTCCCAGG GCATCATCTA CCGGGACCTC      780

AAGCCCGAGA ACATCATGCT CAGCAGCCAG GGCCACATCA AACTGACCGA CTTTGGACTC      840

TGCAAGGAGT CTATCCATGA GGGCGCCGTC ACTCACACCT TCTGCGGCAC CATTGAGTAC      900

ATGGCCCCTG AGATTCTGGT GCGCAGTGGC ACAACCGGG CTGTGGACTG GTGGAGCCTG       960

GGGGCCCTGA TGTACGACAT GCTCACTGGA TCGCCGCCCT TCACCGCAGA GAACCGGAAG     1020

AAAACCATGG ATAAGATCAT CAGGGGCAAG CTGGCACTGC CCCCCTACCT CACCCCAGAT     1080

GCCCGGGACC TTGTCAAAAA GTTTCTGAAA CGGAATCCCA GCCAGCGGAT TGGGGGTGGC     1140

CCAGGGGATG CTGCTGATGT GCAGAGACAT CCCTTTTTCC GGCACATGAA TTGGGACGAC     1200

TTCTGGCCTG GCGTGTGGAN CCCCCTTTCA AGGCCCTGTC TGCAGTCAGA GGAGACGTGA     1260

GCAGTTTGAT ACCCGCTTCA CACGGCAGAC GCCGGTGGAC AGTCCTGATG ACACAGCCTC     1320

AGCGAGAGTG CCAACAAGGC CTTCCTGGGG TTACATAAGT GGCGCGTCTG TCCTGGACAG     1380

ATCAAGAGGT TCTCTTTCAG CCCAAGTGGG TCAACCAGGG CTCAANATAG CCCCGGGTCC     1440

GTNAGCCCCT CAAGTTTNCC CTTTNAGGGT TCGGCCAGCC ACCTTNCNGN GCCAAGGAGT     1500

ACTTACTCAA TCTGCANGGG GNGNNTTGAC AANGCCTTTT CCATCGTCCC CTNAGGGCAA     1560

AATTAAAAGG GCNTGGGTTA AGGNTAGAAC CGGTGGGGTA TAAGNTCCCT TAGCCGTCCT     1620

GGGNTTAAAA NAANNTG                                                    1637
```

(2) INFORMATION FOR SEQ ID NO:11:

(i) SEQUENCE CHARACTERISTICS:
    (A) LENGTH: 1124 base pairs
    (B) TYPE: nucleic acid
    (C) STRANDEDNESS: single
    (D) TOPOLOGY: linear (vii) IMMEDIATE SOURCE:
    (A) LIBRARY: LEUKNOT03
    (B) CLONE: 1880692

(xi) SEQUENCE DESCRIPTION: SEQ ID NO:11:

```
GGAAGAGCAG CGGCGAGGCG GCGGTGGTGG CTGAGTCCGT GGTGGCAGAG GCGAAGGCGA      60

CAGCTCTAGG GGTTGGCACC GGCCCCGAGA GGAGGATGCG GGTCCGGATA GGGCTGACGC     120

TGCTGCTGTG TGCGGTGCTG CTGAGCTTGG CCTCGGCGTC CTCGGATGAA GAAGGCAGCC     180

AGGATGAATC CTTAGATTCC AAGACTACTT TGACATCAGA TGAGTCAGTA AAGGACCATA     240

CTACTGCAGG CAGAGTAGTT GCTGGTCAAA TATTTCTTGA TTCAGAAGAA TCTGAATTAG     300

AATCCTCTAT TCAAGAAGAG GAAGACAGCC TCAAGAGCCA AGAGGGGAA AGTGTCACAG      360

AAGATATCAG CTTTCTAGAG TCTCCAAATC CAGAAAACAA GGACTATGAA GAGCCAAAGA     420

AAGTACGGAA ACCAGCTTTG ACCGCCATTG AAGGCACAGC ACATGGGAG CCCTGCCACT      480

TCCCTTTTCT TTTCCTAGAT AAGGAGTATG ATGAATGTAC ATCAGATGGG AGGGAAGATG     540

GCAGACTGTG GTGTGCTACA ACCTATGACT ACAAAGCAGA TGAAAAGTGG GGCTTTTGTG     600

AAACTGAAGA AGAGGCTGCT AAGAGACGGC AGATGCAGGA AGCAGAAATG ATGTATCAAA     660

CTGGAACGAA AATCCTTAAT GGAAGCAATA AGAAAAGCCA AAAAAGAGAA GCATATCGGT     720

ATCTCCAAAA GGCAGCAAGC ATGAACCATA CCAAAGCCCT GGAGAGAGTG TCATATGCTC     780

TTTTATTTGG TGATTACTTG CCACAGAATA TCCAGGCAGC GAGAGAGATG TTTGAGAAGC     840

TGACTGAGGA AGGCTCTCCC AAGGGACAGA CTGCTCTTGG CTTTCTGTAT GCCTCTGGAC     900

TTGGTGTTAA TTCAAGTCAG GCAAAGGCTC TTGTATATTA TACATTTGGA GCTCTTGGGG     960

GCAATCTAAT AGCCCACATG GTTTTGGGTT ACAGATACTG GGCTGGCATC GGCGTCCTCC    1020

AGAGTTGTGA ATCTGCCCTG ACTCACTATC GTCTTGTTGC CAATCATGGT ATCTATGTTT    1080

CCCCTTTTAC CTTTTAGGAA AAAAAAATAA ATGGAATTAA CTTT                     1124
```

(2) INFORMATION FOR SEQ ID NO:12:

(i) SEQUENCE CHARACTERISTICS:
        (A) LENGTH: 1452 base pairs
        (B) TYPE: nucleic acid
        (C) STRANDEDNESS: single
        (D) TOPOLOGY: linear (vii) IMMEDIATE SOURCE:
        (A) LIBRARY: EOSIHET02
        (B) CLONE: 318060

(xi) SEQUENCE DESCRIPTION: SEQ ID NO:12:

```
CANCAGGTGT TTATTAGGGT CCTTTTTCAT TACCCCAGAG ACAGACCCAG GGCTGGCTAC      60

GTGCACAGGA AGTAACGCTT GCCACATGCA TAAATACGTG AAGGTGCACA TTACATCAGC     120

ACAGATTCAC AAAACACCTC GCCTTGGCAA GAAAACTGTA GCTAGGCAGC TCCCGTCCTC     180

AGGGACTCCT GCCACAGACG TCATGGAGAC AGCATGAGCC TCCCCAGAAC AGTCCCCACG     240

GCCTAGACTC CCCAGAGCAG GAGGAGCAGC CCAGGCTCTG TTGCGAGACA GCCATCACTT     300

CCTGTTCTTT GCAGGTGCCT AAGGTAGGTT ACCTGGCCAA GGTTTTGGTG GAAAAAATGA     360

GTTTTTTCAA TGTTGCAGGT CTTTTAATAG TTCATCTGTA GGAAGTGCAT TTGCAAAGTC     420

ACCAACCTGC AGCTTCCATC TGTAGACCAG GAAGGGTGAT TCTCTGGGTG ANCACAGCGG     480
```

```
GGCNTNCCCT GAGGTACANA NNTNCCCNCC CANACCCCCG CAGTGTCCTC ACAGCCATCA      540

CAGGCTTTGG AAGTTTGGCT CAAGCAAGGC CNTTGCNAAG GCCCCCAACC CCCTTCATGG      600

TTGGGCTTCT GCTGTGAAAG CCAATCCCTC CCGGTTNGGG CNAGCNAAGN TCAANGGGCC      660

TTACCCCANG AGGCCATTCT TGAAGGGNTT GTAAAATNGA AGCAGGAAGC TGTGTGGAAG      720

GAGAAGCTGG TGGCCACAGC AGAGTCCTGC TCTGGGACG CCTGCTTCAT TTACAAGCCT      780

CAAGATGGCT CTGTGTAGGG CCTGAGCTTG CTGCCCAACG GGAGGATGGC TTCACAGCAG      840

AGCCAGCATG AGGGGTGGGG CCTGGCAGGG CTTGCTTGAG CCAAACTGCA AAGGCTGTGG      900

TGGCTGTGAG GACACTGCGG GGGTTGGGGG GGGGCGTCTG TACCTCAGGG GATGCCCCGC      960

TGTGGTCACC CAGAGAATCA CCCTTCCTGG TCTACAGATG GAAGCTGCAG GTTGGTGACT     1020

TTGCAAATGC ACTTCCTACA GATGAACTAT TAAAAGACCT GCAACATTGA AAAAACTCAT     1080

TTTTTCCACC AAAACCTTGG CCAGGTAACC TACCTTAGGC ACCTGCAAAG AACAGGAAGT     1140

GATGGCTGTC TCGCAACAGA GCCTGGGCTG CTCCTCCTGC TCTGGGAGT CTAGGCCGTG     1200

GGGACTGTTC TGGGGAGGCT CATGCTGTCT CCATGACGTC TGTGGCAGGA GTCCCTGAGG     1260

ACGGGAGCTG CCTAAGCTAC AGTTTTTYTT SCCAAGGGCG AGGTGTTTTG TGAATCTGTG     1320

CTGATGTAAT GTGCACCTTC ACGTATTTAT GCATGTGGCA AGCGTTACTT CCTGTGCACG     1380

TAGCCAGCCC TGGGTCTGTC TCTGGGGTAA TGAAAAAGGA CCCTAATAAA CACCTGCTCA     1440

CTGGCTGGGT GG                                                         1452

(2) INFORMATION FOR SEQ ID NO:13:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (vii) IMMEDIATE SOURCE:
        (A) LIBRARY: PITUNOT02
        (B) CLONE: 396450

(xi) SEQUENCE DESCRIPTION: SEQ ID NO:13:

GGGGAAGAAG AGCCGCGANC GAGAGAGGNC GGCGAGCGTC CCNGGCCTNA GAGAGCAGCC       60

TCCCGAGANA GGCANTTGCT GGATTNTCCA AAAGTATCTG CAGTGGCTGT TNCANCAGGA      120

GAGCCTCAGN CTGCCTGGAA GATGCCGAGA TCGTGCTGCA GCCGCTCGGG GGCCCTGTTG      180

CTGGNCTTGC TGCTTCAGGN CTCCATGGAA GTGCGTGGCT GGTGCCTGGA GAGCAGCCAG      240

TGTNAGGACC TNANCAAGGA AAGCAANCTG CTTGAGTNCA                            280

(2) INFORMATION FOR SEQ ID NO:14:

(i) SEQUENCE CHARACTERISTICS:
        (A) LENGTH: 514 base pairs
        (B) TYPE: nucleic acid
        (C) STRANDEDNESS: single
        (D) TOPOLOGY: linear (vii) IMMEDIATE SOURCE:
        (A) LIBRARY: TMLR3DT02
        (B) CLONE: 506333

(xi) SEQUENCE DESCRIPTION: SEQ ID NO:14:

TGTGGAGTCA GCCCAGTCTG GATGCACAGG AGGATGCTGG CGGCACAGTG AGTGAGGCCT       60

GGTGCCAGAG CTGTGCGGAC CCCTTGTTGG CCATGGAGCA GCAGGCCCAG AGGCCCTCTC      120

CCCAGCCCTG CTTGCCTGCC TCGGAGAGGA CAGAGGCCTA GCCCACGGG GGAGGGTGTT      180
```

```
GGCAGACAGA TGCCCTCCAG GCCCTGGGGC CTCCTTAACG GCCCCTTAAC GACACGCGTG      240

CCAAGGGTGG AGGATGCCAG CCAAGGGGCG CTACTTCCTC AACGAGGGCG AGGAGGGCCC      300

TGACCAAGAT GCGCTCTACG AGAAGTACCA GCTCACCAGC CAGCATGGGC CGCTGCTGCT      360

CACGCTCCTG CTGGTGGNCG CAATGCCTGC GTNGCCCTCA TCATATTGCC TCAGCCAGGG      420

GGTGAGTNAA GGCAGCCCTT GGGNTCAAGT CTCGGCCCAN ACTTTGGCAA GTGCTATCTT      480

CTCTTAGCTC TTCTGAAAAT GCTTATCTTC TGTA                                  514

(2) INFORMATION FOR SEQ ID NO:15:

(i) SEQUENCE CHARACTERISTICS:
        (A) LENGTH: 617 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT04
        (B) CLONE: 764465

(xi) SEQUENCE DESCRIPTION: SEQ ID NO:15:

AAACTACATT TTGCAAAGTC ATTGAACTCT GAGCTCAGTT GCAGTACTCG GGAAGCCATG       60

CAGGATGAAG ATGGATACAT CACCTTAAAT ATTAAAACTC GGAAACCAGC TCTCGTCTCC      120

GTTGGCCCTG CATCCTCCTC CTGGTGGCGT GTGATGGCTT TGATTCTGCT GATCCTGTGC      180

GTGGGGATGG TTGTCGGGCT GGTGGCTCTG GGGATTTGGT CTGTCATGCA GCGCAATTAC      240

CTACAAGATG AGAATGAAAA TCGCACAGGA ACTCTGCAAC AATTAGCAAA GCGCTTCTGT      300

CAATATGTGG TAAAACAATC AGAACTAAAA GGGCACTTTC AAAGGTCATA AATGCAGCCC      360

CTGTGACACA AACTGGAGAT ATTATGGAGA TAGCTGCTAT GGGTTCTTCA GGCACAACTT      420

AACATGGGAA GAGAGTAAGC AGTACTGCAC TGACATGAAT GCTACTCTCC TGAAGATTGA      480

CAACCGGAAC ATTGTGGAGT ACATCAAAGC CAGGACTCAT TTAATTCGTT TGGGTCNGAT      540

TATCTCGCCA GAAGTCGAAT GAGGTCTGGA AGTGGGANGA TGGCTCGGGT ATCTCAGNAA      600

ATATGNTTGA GTTTTTG                                                     617

(2) INFORMATION FOR SEQ ID NO:16:

(i) SEQUENCE CHARACTERISTICS:
        (A) LENGTH: 350 amino acids
        (B) TYPE: amino acid
        (C) STRANDEDNESS: single
        (D) TOPOLOGY: linear (vii) IMMEDIATE SOURCE:
        (A) LIBRARY: UTRSNOT11
        (B) CLONE: 2547002

(xi) SEQUENCE DESCRIPTION: SEQ ID NO:16:

Met Ala Leu Glu Gln Asn Gln Ser Thr Asp Tyr Tyr Tyr Glu Asn
1               5                  10                  15

Glu Met Asn Gly Thr Tyr Asp Tyr Ser Gln Tyr Glu Leu Ile Cys Ile
                20                  25                  30

Lys Glu Asp Val Arg Glu Phe Ala Lys Val Phe Leu Pro Val Phe Leu
        35                  40                  45

Thr Ile Val Phe Val Ile Gly Leu Ala Gly Asn Ser Met Val Val Ala
    50                  55                  60

Ile Tyr Ala Tyr Tyr Lys Lys Gln Arg Thr Lys Thr Asp Val Tyr Ile
```

```
             65                  70                  75                  80
Leu Asn Leu Ala Val Ala Asp Leu Leu Leu Phe Thr Leu Pro Phe
                        85                  90                  95
Trp Ala Val Asn Ala Val His Gly Trp Val Leu Gly Lys Ile Met Cys
                100                 105                 110
Lys Ile Thr Ser Ala Leu Tyr Thr Leu Asn Phe Val Ser Gly Met Gln
            115                 120                 125
Phe Leu Ala Cys Ile Ser Ile Asp Arg Tyr Val Ala Val Thr Lys Val
        130                 135                 140
Pro Ser Gln Ser Gly Val Gly Lys Pro Cys Trp Ile Ile Cys Phe Cys
145                 150                 155                 160
Val Trp Met Ala Ala Ile Leu Leu Ser Ile Pro Gln Leu Val Phe Tyr
                165                 170                 175
Thr Val Asn Asp Asn Ala Arg Cys Ile Pro Ile Phe Pro Arg Tyr Leu
            180                 185                 190
Gly Thr Ser Met Lys Ala Leu Ile Gln Met Leu Glu Ile Cys Ile Gly
        195                 200                 205
Phe Val Val Pro Phe Leu Ile Met Gly Val Cys Tyr Phe Ile Thr Ala
    210                 215                 220
Arg Thr Leu Met Lys Met Pro Asn Ile Lys Ile Ser Arg Pro Leu Lys
225                 230                 235                 240
Val Leu Leu Thr Val Val Ile Val Phe Ile Val Thr Gln Leu Pro Tyr
                245                 250                 255
Asn Ile Val Lys Phe Cys Arg Ala Ile Asp Ile Ile Tyr Ser Leu Ile
            260                 265                 270
Thr Ser Cys Asn Met Ser Lys Arg Met Asp Ile Ala Ile Gln Val Thr
        275                 280                 285
Glu Ser Ile Ala Leu Phe His Ser Cys Leu Asn Pro Ile Leu Tyr Val
    290                 295                 300
Phe Met Gly Ala Ser Phe Lys Asn Tyr Val Met Lys Val Ala Lys Lys
305                 310                 315                 320
Tyr Gly Ser Trp Arg Arg Gln Arg Gln Ser Val Glu Glu Phe Pro Phe
                325                 330                 335
Asp Ser Glu Gly Pro Thr Glu Pro Thr Ser Thr Phe Ser Ile
            340                 345                 350
```

(2) INFORMATION FOR SEQ ID NO:17:

(i) SEQUENCE CHARACTERISTICS:
        (A) LENGTH: 1660 base pairs
        (B) TYPE: nucleic acid
        (C) STRANDEDNESS: single
        (D) TOPOLOGY: linear (vii) IMMEDIATE SOURCE:
        (A) LIBRARY: UTRSNOT11
        (B) CLONE: 2547002

(xi) SEQUENCE DESCRIPTION: SEQ ID NO:17:

```
GCGACGTACA ACAGATTGGA GCCATGGCTT TGGAACAGAA CCAGTCAACA GATTATTATT      60

ATGAGGAAAA TGAAATGAAT GGCACTTATG ACTACAGTCA ATATGAACTG ATCTGTATCA     120

AAGAAGATGT CAGAGAATTT GCAAAAGTTT TCCTCCCTGT ATTCCTCACA ATAGTTTTCG     180

TCATTGGACT TGCAGGCAAT TCCATGGTAG TGGCAATTTA TGCCTATTAC AAGAAACAGA     240

GAACCAAAAC AGATGTGTAC ATCCTGAATT TGGCTGTAGC AGATTTACTC CTTCTATTCA     300

CTCTGCCTTT TTGGGCTGTT AATGCAGTTC ATGGGTGGGT TTTAGGGAAA ATAATGTGCA     360
```

```
AAATAACTTC AGCCTTGTAC ACACTAAACT TTGTCTCTGG AATGCAGTTT CTGGCTTGTA        420

TCAGCATAGA CAGATATGTG GCAGTAACTA AAGTCCCCAG CCAATCAGGA GTGGGAAAAC        480

CATGCTGGAT CATCTGTTTC TGTGTCTGGA TGGCTGCCAT CTTGCTGAGC ATACCCCAGC        540

TGGTTTTTTA TACAGTAAAT GACAATGCTA GGTGCATTCC CATTTTCCCC CGCTACCTAG        600

GAACATCAAT GAAAGCATTG ATTCAAATGC TAGAGATCTG CATTGGATTT GTAGTACCCT        660

TTCTTATTAT GGGGGTGTGC TACTTTATCA CAGCAAGGAC ACTCATGAAG ATGCCAAACA        720

TTAAAATATC TCGACCCCTA AAAGTTCTGC TCACAGTCGT TATAGTTTTC ATTGTCACTC        780

AACTGCCTTA TAACATTGTC AAGTTCTGCC GAGCCATAGA CATCATCTAC TCCCTGATCA        840

CCAGCTGCAA CATGAGCAAA CGCATGGACA TCGCCATCCA AGTCACAGAA AGCATCGCAC        900

TCTTTCACAG CTGCCTCAAC CCAATCCTTT ATGTTTTTAT GGGAGCATCT TTCAAAAACT        960

ACGTTATGAA AGTGGCCAAG AAATATGGGT CCTGGAGAAG ACAGAGACAA AGTGTGGAGG       1020

AGTTTCCTTT TGATTCTGAG GGTCCTACAG AGCCAACCAG TACTTTTAGC ATTTAAAGGT       1080

AAAACTGCTC TGCCTTTTGC TTGGATACAT ATGAATGATG CTTTCCCCTC AAATAAAACA       1140

TCTGCATTAT TCTGAAACTC AAATCTCAGA CGCCGTGGTT GCAACTTATA ATAAAGAATG       1200

GGTTGGGGGA AGGGGGAGAA ATAAAAGCCA AGAAGAGGAA ACAAGATAAT AAATGTACAA       1260

AACATGAAAA TTAAAATGAA CAATATAGGA AAATAATTGT AACAGGCATA AGTGAATAAC       1320

ACTCTGCTGT AACGAAGAAG AGCTTTGTGG TGATAATTTT GTATCTTGGT TGCAGTGGTG       1380

CTTATACAAA TCTACACAAG TGATAAAATG ACAGAGAACT ATATACACAC ATTGTACCAA       1440

TTTCAATTTC CTGGTTTTGA CATTATAGTA TAATTATGTA AGATGGAACC ATTGGGGAAA       1500

ACTGGGTGAA GGGTACCCAG GACCACTCTG TACCATCTTT GTAACTTCCT GTGAATTTAT       1560

AATAATTTCA AAATAAAACA AGTTAAAAAA AAAACCCACT ATGCTATAAG TTAGGCCATC       1620

TAAAACAGAT TATTAAAGAG GTTCATGTTA AAAGGCATGC                             1660
```

(2) INFORMATION FOR SEQ ID NO:18:

(i) SEQUENCE CHARACTERISTICS:
        (A) LENGTH: 350 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 399711

(xi) SEQUENCE DESCRIPTION: SEQ ID NO:18:

```
Met Ala Val Glu Tyr Asn Gln Ser Thr Asp Tyr Tyr Glu Asn
  1               5                  10                  15

Glu Met Asn Asp Thr His Asp Tyr Ser Gln Tyr Glu Val Ile Cys Ile
                 20                  25                  30

Lys Glu Glu Val Arg Lys Phe Ala Lys Val Phe Leu Pro Ala Phe Phe
         35                  40                  45

Thr Ile Ala Phe Ile Ile Gly Leu Ala Gly Asn Ser Thr Val Val Ala
     50                  55                  60

Ile Tyr Ala Tyr Tyr Lys Lys Arg Arg Thr Lys Thr Asp Val Tyr Ile
 65                  70                  75                  80

Leu Asn Leu Ala Val Ala Asp Leu Phe Leu Phe Thr Leu Pro Phe
                 85                  90                  95

Trp Ala Val Asn Ala Val His Gly Trp Val Leu Gly Lys Ile Met Cys
                100                 105                 110
```

-continued

```
Lys Val Thr Ser Ala Leu Tyr Thr Val Asn Phe Val Ser Gly Met Gln
        115                 120                 125

Phe Leu Ala Cys Ile Ser Thr Asp Arg Tyr Trp Ala Val Thr Lys Ala
        130                 135                 140

Pro Ser Gln Ser Gly Val Gly Lys Pro Cys Trp Val Ile Cys Phe Cys
145                 150                 155                 160

Val Trp Val Ala Ala Ile Leu Leu Ser Ile Pro Gln Leu Val Phe Tyr
                165                 170                 175

Thr Val Asn His Lys Ala Arg Cys Val Pro Ile Phe Pro Tyr His Leu
                180                 185                 190

Gly Thr Ser Met Lys Ala Ser Ile Gln Ile Leu Glu Ile Cys Ile Gly
        195                 200                 205

Phe Ile Ile Pro Phe Leu Ile Met Ala Val Cys Tyr Phe Ile Thr Ala
        210                 215                 220

Lys Thr Leu Ile Lys Met Pro Asn Ile Lys Lys Ser Gln Pro Leu Lys
225                 230                 235                 240

Val Leu Phe Thr Val Val Ile Val Phe Ile Val Thr Gln Leu Pro Tyr
                245                 250                 255

Asn Ile Val Lys Phe Cys Gln Ala Ile Asp Ile Ile Tyr Ser Leu Ile
                260                 265                 270

Thr Asp Cys Asp Met Ser Lys Arg Met Asp Val Ala Ile Gln Ile Thr
        275                 280                 285

Glu Ser Ile Ala Leu Phe His Ser Cys Leu Asn Pro Val Leu Tyr Val
        290                 295                 300

Phe Met Gly Thr Ser Phe Lys Asn Tyr Ile Met Lys Val Ala Lys Lys
305                 310                 315                 320

Tyr Gly Ser Trp Arg Arg Gln Arg Gln Asn Val Glu Glu Ile Pro Phe
                325                 330                 335

Glu Ser Glu Asp Ala Thr Glu Pro Thr Ser Thr Phe Ser Ile
                340                 345                 350
```